(12) United States Patent
Esteves et al.

(10) Patent No.: US 11,332,762 B2
(45) Date of Patent: May 17, 2022

(54) MICROBIAL PROCESSING OF GASES

(71) Applicant: USW Commercial Services Ltd, Pontypridd (GB)

(72) Inventors: Sandra Esteves, Pontypridd (GB); Richard Mark Dinsdale, Pontypridd (GB); Timothy Patterson, Pontypridd (GB); Savvas Savvas, Pontypridd (GB)

( * ) Notice: Subject to any disclaimer, the term of this patent is extended or adjusted under 35 U.S.C. 154(b) by 1120 days.

(21) Appl. No.: 15/637,206

(22) Filed: Jun. 29, 2017

(65) Prior Publication Data
US 2017/0314045 A1 Nov. 2, 2017

Related U.S. Application Data

(63) Continuation of application No. PCT/GB2015/054176, filed on Dec. 30, 2015.

(30) Foreign Application Priority Data

Dec. 30, 2014 (GB) .................................... 1423363

(51) Int. Cl.
| | |
|---|---|
| *C12P 5/02* | (2006.01) |
| *C12N 1/20* | (2006.01) |
| *C12M 1/107* | (2006.01) |
| *C12M 1/00* | (2006.01) |
| *C12M 1/34* | (2006.01) |

(52) U.S. Cl.
CPC .............. *C12P 5/023* (2013.01); *C12M 21/04* (2013.01); *C12M 29/00* (2013.01); *C12M 41/44* (2013.01); *C12N 1/20* (2013.01); *Y02E 50/30* (2013.01)

(58) Field of Classification Search
CPC ........ C12P 5/023; C12M 21/04; C12M 29/00; C12M 41/44; C12N 1/20; Y02E 50/343; Y02E 50/30
See application file for complete search history.

(56) References Cited

U.S. PATENT DOCUMENTS

| 8,741,142 B1 | 6/2014 | Cook | |
|---|---|---|---|
| 2009/0221027 A1* | 9/2009 | Zelder | ............... C12P 7/06 435/69.1 |
| 2014/0011251 A1* | 1/2014 | Mets | ............... C12M 21/04 435/167 |

FOREIGN PATENT DOCUMENTS

| EP | 0642470 B1 | 11/1998 | |
|---|---|---|---|
| EP | 2135938 A1 | 12/2009 | |
| EP | 2208712 A1 | 7/2010 | |
| GB | 2477422 A | 8/2011 | |
| WO | 2011073618 A2 | 6/2011 | |
| WO | 2013060331 A1 | 5/2013 | |
| WO | 2014128300 A1 | 8/2014 | |
| WO | WO-2014128300 A1 * | 8/2014 | ............ C12M 23/58 |
| WO | 2014210071 A1 | 12/2014 | |

OTHER PUBLICATIONS

O'Flaherty, Vincent et al. Anaerobic Digestion of Agricultural Residues. Environmental Microbiology, Second Edition Edited by Ralph Mitchell and Ji-Dong Gu Copyright© 2010 Wiley-Blackwell. pp. 265-285. (Year: 2010).*

D'Flaherty et al., Anaerobic digestion of agricultural residues' Mitchell, R and Gu, J-D: Environmental microbiology 2010, Wiley-Blackwell, Hoboken, New Jersey, pp. 265-285, the whole document.

* cited by examiner

*Primary Examiner* — Susan M Hanley
(74) *Attorney, Agent, or Firm* — EIP US LLP

(57) ABSTRACT

The invention includes methods, apparatus, and systems for the conversion of hydrogen together with carbon dioxide or carbon monoxide to methane using a population of microbes and a defined liquid medium. The microbial population maintains the amount of nutrients in the liquid medium within a relative range without requiring replenishment of the nutrients. Methods and apparatus for enriching the microbial population are also described.

11 Claims, 21 Drawing Sheets

| Values in mg/l (TS=1%) | Al | B | Ca | Co | Cu | Fe | K | Mg | Mn | Mo | Na | Ni | P | S | Se | Zn | W |
|---|---|---|---|---|---|---|---|---|---|---|---|---|---|---|---|---|---|
| 29-Jul | 115.61 | 0.43 | 257.54 | 0.09 | 2.69 | 188.26 | 76.83 | 59.26 | 4.69 | 0.93 | 49.52 | 3.78 | 148.73 | 102.97 | <0.02 | 7.59 | <0.02 |
| 06-Aug | 131.69 | 0.08 | 252.04 | 0.09 | 3.06 | 176.52 | 78.28 | 63.82 | 5.64 | 1.23 | 43.24 | 4.16 | 155.27 | 123.79 | <0.02 | 8.73 | <0.02 |
| 11-Oct | 117.45 | 0.37 | 244.85 | 0.10 | 2.83 | 179.46 | 89.35 | 59.98 | 4.95 | 1.42 | 56.84 | 5.44 | 148.38 | 109.21 | <0.02 | 7.48 | <0.02 |

FIG. 11

| Element | mg/l of element; suggest minimum requirements | Example of chemical used |
|---|---|---|
| Na | 50.00 | $NaHCO_3$ |
| K | 50.00 | KCl |
| Mg | 20.00 | $MgCl_2$ |
| Ca | 2.00 | $CaCl_2$ |
| P | 25.00 | $KH_2PO_4$ |
| S | 25.00 | Cysteine-Cl |
| N | 100.00 | $NH_4Cl$ |
| Fe | 0.50 | $FeCl_2$ |
| Co | 0.05 | $CoCl_2$ |
| Cu | 0.01 | $CuCl_2$ |
| Mn | 0.05 | $MnCl_2$ |
| Mo | 0.05 | $Na_2MoO_4$ |
| Ni | 0.05 | $NiCl_2$ |
| Se | 0.05 | $SeCl_4$ |
| W | 0.05 | $NaWO_4$ |
| B | 0.01 | $H_3BO_3$ |
| Al | 0.01 | $Al_2(SO_4)$ |
| Zn | 0.03 | $ZnSO_4$ |
| V | 0.03 | $VCl_3$ |

FIG. 12

MICROBIAL PROCESSING OF GASES

CROSS-REFERENCE TO RELATED APPLICATIONS

This application is a continuation of International Patent Application No. PCT/GB2015/054176, filed on Dec. 30, 2015, which claims the benefit of U.K. Application GB 1423363.9, filed on Dec. 30, 2014. Each of the above-referenced patent applications is incorporated by reference in its entirety.

BACKGROUND OF THE INVENTION

Field of the Invention

The present invention relates to methods and apparatus for microbial conversion of carbon dioxide, carbon monoxide and hydrogen to methane, and to the microbial populations, and the media comprising the microbial populations, that may be used in such methods and apparatus.

Description of the Related Technology

There is an increasing requirement to embed low carbon renewable energy systems in the global energy supply network to reduce the global emissions of carbon dioxide. Renewable energy sources such as wind, wave and solar power, and alternative sources of fuel are increasingly used; however, these sources are not fully dispatchable and some energy storage mechanism is very likely to be required as these sources of energy increase as a percentage of the global energy supply.

Meanwhile, gases such as biogas from anaerobic digestion, gasification/pyrolysis gas, coal bed gas, coke oven gas and landfill gas can contain significant contaminants or by-products such as carbon dioxide, hydrogen and carbon monoxide. For these gases to be used in the existing natural gas and conventional energy utilisation technologies these contaminants need to be removed or converted.

The largest contaminant in these gases is normally carbon dioxide. For example, the methane content of biogas from anaerobic digestion is typically around 55-70% by volume of the total gas produced, with the largest remaining fraction being carbon dioxide. Various methods have been used in order to increase the methane content of the biogas, in particular so that the end product may reach the equivalent quality of natural gas, by removing carbon dioxide from the biogas. Such methods include: absorption of the carbon dioxide in water or organic solvents, or via other means of chemical absorption; via pressure swing adsorption of carbon dioxide with activated carbon or zeolites; membrane separation; and cryogenic separation. This means however that between 30-45% of the carbon is not utilised and is released to the atmosphere. For syngas the removal of carbon monoxide is also required and some of these technologies, such as membrane separation, can be used to achieve this.

An alternative to separating out the carbon dioxide or carbon monoxide is to convert it to methane. This may be done via means of the Sabatier reaction. This converts carbon dioxide and hydrogen to methane, by utilising high temperatures (e.g. between about 300 and 400° C.) in combination with a metal catalyst (e.g. Ni, Ru). This can achieve conversion efficiencies of up to 80%. (Murphy, J. D., Browne, J., Allen, E. & Gallagher, C. (2013). *The resource of biomethane, produced via biological, thermal and electrical routes, as a transport biofuel*. Renewable Energy, 55, 474-479). However, to date there are a number of issues that prevent its commercialisation. The catalysts are expensive and their activity tends to decrease over time so regeneration is needed. Only high purity biogases may be used as a starting material as any pollutants such as hydrogen sulphide lead to catalyst deactivation (Wang, W., Wang, S., Ma, X. & Gong, J. (2011). *Recent advances in catalytic hydrogenation of carbon dioxide*. Chem. Soc. Rev., 40, 3703-3727). Furthermore, because the reaction is highly exothermic the removal of the extra heat can be challenging as the temperature needs to be maintained and evenly distributed without creating hot spots which then repress the reaction (Brooks, K. P., Hu, J., Zhu, H. & Kee, R. J. (2007). *Methanation of carbon dioxide by hydrogen reduction using the Sabatier process in microchannel reactors*. Chemical Engineering Science 62, 1161-1170). The economic feasibility of large scale plants is still ambiguous as it largely depends on the correct utilization of the produced thermal energy (Hoekman, S. K., Broch, A., Robbins, C. & Purcell, R. (2010). *CO2 recycling by reaction with renewably-generated hydrogen*. International Journal of Greenhouse Gas Control 4, 44-50). It also depends on improvements of catalytic systems in order to overcome current disparities like low selectivities, low yields and deactivation (Wang et al., 2011, as above).

Meanwhile, alternative sources of energy face other problems. In particular, the natural variance in the availability of solar, tidal or wind power means that systems utilising these sources for energy production are prone to periods of under- and over-supply of energy. For example, countries with an increasing growth in wind energy like Germany, Denmark and the UK have already started to experience problems regarding power management (Linnemann, J. & Steinberger-Wilckens, R. (2006). *Realistic costs of wind-hydrogen vehicle fuel production*. International Journal of Hydrogen Energy, 32, 1492-1499). In particular, when power generation exceeds network capacity, curtailment of power generation is often the only option. According to NREL (NREL (2013). *Wind and Solar Curtailment*. Conference paper presented at the International Workshop on Large-Scale Integration of Wind Power Into Power Systems as Well as on Transmission Networks for Offshore Wind Power Plants. London, England Oct. 22-24, 2013; Available at: http://www.osti.gov/bridge), by 2030 due to a significant increase in wind penetration, curtailment in northern Europe is expected to reach 9.3 TWh.

For example, a statistical analysis carried out by Black and Strbac (Black, M. And Strbac, G. (2006). *Value of storage in providing balancing services for electricity generation systems with high wind penetration*. Journal of Power Sources, 162, 949-953), showed that during a 4 hour period the magnitude of change in wind power output can easily reach 37%. In order for a 10 MW (small scale) system to compensate for these fluctuations it would need to have a reserve capacity that would allow for an immediate 3.7 MW production. As fluctuations increase over longer periods of time, the reserve capacity of the compensatory system will ultimately need to be capable of the same power output as the renewable generator. For large wind farms (>50 MW), currently this is only possible for pumped hydroelectric storage and underground compressed air storage (Gonzalez, A., Gallachoir, B., McKeogh, E. & Lynch, K. (2004). *Study of Electricity Storage Technologies and Their Potential to Address Wind Energy Intermittency in Ireland*. Final Report. Project Funded by the National Development Plan through Sustainable Energy Ireland's Renewable Energy Research, Development and Demonstration Grant RE/HC/03/001; Available at: http://www.seai.ie), both of which are systems limited by geographical factors. Batteries are unsuitable and need an increased life time and depth of discharge accompanied with a reduction in production costs (Barnhart, C. J., Dale, M., Brandt, A. R. & Benson, S. M. (2013). *The energetic implications of curtailing versus storing solar-and wind-generated electricity*. Energy Environ. Sci., 6, 2804-2810). Super capacitors, superconducting coils and flywheels have a very short discharge period which makes them suitable only as emergency uninterruptible power system ("UPS") units (Gonzalez et al., 2004, as above).

The use of hydrogen is a possible solution as it can be used either in fuel cells or in combustion engines; however there are still issues with its long term storage and fuel cell power systems for large applications are still at the research stage (He, C., Desai, S., Brown, G. & Bollepalli, S. (2005). *PEM Fuel Cell Catalysts: Cost, Performance, and Durability*. The Electrochemical Society Interface; available at: http://www.electrochem.org).

The use of biomethanation presents a solution to these problems and can also be used to upgrade biogases contaminated with carbon dioxide and carbon monoxide. As for other forms of alternative energy sources, the creation of methane provides a potential means of energy capture and storage. Methane is particularly suitable as a form of energy storage. The infrastructure for its usage and transport already exists, it can be safely stored for long periods without losses, and its production and usage is not limited to geographical factors.

Biomethanation has a similar aim to the Sabatier process, with the significant difference that the catalysis is provided by anaerobic hydrogenotrophic methanogens. This provides a number of advantages: it allows for the reaction to happen at lower temperatures than in the Sabatier process; it does not require catalysts comprising expensive metals and alloys; and reaction selectivity is an inherent feature of the microbes involved. Also, since the carbon dioxide required by the bioconversion system is a common by-product of many industries, its conversion to methane could be considered as a form of carbon capture. However, as with Sabatier methanation, the process requires hydrogen which is used by hydrogenotrophs as an electron donor.

Two main groups of methanogenic archaea are commonly used in anaerobic digestion systems, namely acetoclastic methanogens and hydrogenotrophic methanogens. In naturally occurring systems, such as in the digestive tracts of ruminant animals, these two types of methanogenic archaea operate syntrophically with hydrolytic, acidogenic, and acetogenic bacteria. The hydrolytic bacteria enable the conversion of large molecules, such as carbohydrates, lipids and proteins, into monomers or short chains, such as sugars, fatty acids and amino acids. These are in turn converted to intermediates such as formate, butyrate, valerate, propionate, acetate, carbon dioxide, hydrogen, and ethanol by the acidogenic bacteria, and a number of the intermediates are then converted to acetate by acetogenic bacteria. The other products of the hydrolysis, acidogenesis and acetogenesis are hydrogen and carbon dioxide. The acetoclastic methanogens utilise the acetate to produce methane, and the hydrogenotrophic methanogens produce methane from the hydrogen and carbon dioxide. Consequently, in natural systems, the combination of acetoclastic and hydrogenotrophic methanogens is required. In anaerobic digesters when hydrogen concentrations are increased it is usually a sign of metabolic and process failure. The addition of extra hydrogen for in-situ conversion of the carbon dioxide into methane would therefore lead to a degradation of digester performance. Control over pH would also be challenging and the continual loss of microbial community with the removal of digested materials would make these systems inefficient.

Some more recent known systems utilise separate vessels located away from the anaerobic digestion of organics. Conversion of hydrogen and carbon dioxide via biomethanation has been previously performed with a selected one-culture microbe *Methanothermobacter thermautotrophicus* ΔH (Martin, M., Fornero, J., Stark, R., Mets, L. & Angenent. (2013). *A Single-Culture Bioprocess of Methanothermobacter thermautotrophicus to Upgrade Digester Biogas by CO2-to-CH4 Conversion with H2*. Archaea, Volume 2013, Article ID 157529), or via a thermophilic microbial culture (Luo, G. & Angelidaki, I. (2012). *Integrated Biogas Upgrading and Hydrogen Utilization in an Anaerobic Reactor Containing Enriched Hydrogenotrophic Methanogenic Culture*. Biotechnology and Bioengineering, 109, No. 11, 2729-2736); these systems however, require a continual input of nutrients and trace elements and a continual need to grow the microbes due to dilution and removal of water from the system. Such known systems also produce undesirably low outputs.

To date, only a few attempts have been made to produce biomethanation systems, which have achieved variable efficiencies. Process efficiency has been stated to relate to microbial density. WO 2014/128300 A1 discloses that the volumetric methane productivity of a biomethanation reactor is directly proportional to the biomass density, i.e. the concentration of methanogenic cells, within the reactor. Nevertheless, there remains a need for methods and means for the efficient production of methane via biomethanation.

SUMMARY

According to a first aspect of the present invention, there is provided a medium comprising a population of microbial organisms, wherein the microbial population comprises: one or more species of hydrogenotrophic methanogens; one or more species of hydrolytic microbes; one or more species of acidogenic microbes, one or more species of acetogenic microbes; and one or more species of acetoclastic microbes, and wherein the medium comprises one or more nutrients comprising at least one of: aluminium, wherein the aluminium is present in an amount of at least about 0.01 mg/l; boron, wherein the boron is present in an amount of at least about 0.01 mg/l; calcium, wherein the calcium is present in an amount of at least about 2.0 mg/l; cobalt, wherein the cobalt is present in a range of between about 0.05 mg/l and about 1 mg/l; copper, wherein the copper is present in a range of between about 0.01 mg/l and about 4 mg/l; iron, wherein the iron is present in an amount of at least about 0.5 mg/l; potassium, wherein the potassium is present in an amount of at least about 50 mg/l; magnesium, wherein the magnesium is present in an amount of at least about 20 mg/l; manganese, wherein the manganese is present in a range of about 0.05 mg/l and about 6 mg/l; molybdenum, wherein the molybdenum is present in a range of about 0.05 mg/l and 1.5 mg/l; nickel, wherein the nickel is present in a range of about 0.05 mg/l and 6 mg/l; phosphorus, wherein the phosphorus is present in an amount of at least about 25 mg/l; sulphur, wherein the sulphur is present in an amount of at least about 25 mg/l; selenium, wherein the selenium is present in a range of about 0.05 mg/l and about 1.5 mg/l; sodium, wherein the sodium is present in an amount of at least about 40 mg/l; tungsten, wherein the tungsten is present in a range of about 0.05 mg/l and about 1.5 mg/l; vanadium, wherein the vanadium is present in a range of about 0.03 mg/l and about 1.5 mg/l and zinc, wherein the zinc is present in a range of about 0.03 mg/l and about 9 mg/l; and wherein the microbial population is capable of maintaining the amount of the one or more nutrients in the medium within the range relative to the amount of water and total solids within the medium, without the addition of the one or more nutrients to the medium. Nitrogen levels will also be largely maintained except for traces leaving with the gas output. Nitrogen may be present above 100 mg/l.

In one embodiment, the medium comprises at least two of the nutrients in an amount within the ranges. In one embodiment, the at least two nutrients are sodium and potassium.

In one embodiment, the medium comprises at least five of the nutrients in an amount within the ranges. In one embodiment, the at least five nutrients are magnesium, calcium, phosphorus, sulphur and iron.

In one embodiment, the medium comprises at least nine of the nutrients in an amount within the ranges. In one embodiment, the at least nine nutrients are cobalt, copper, manganese, molybdenum, nickel, selenium, tungsten, boron and aluminium.

In one embodiment, the medium comprises eighteen of the nutrients in an amount within the ranges.

In one embodiment, during the period during which the microbial population is capable of maintaining the amount of the one or more nutrients in the medium within the range relative to the amount of water and total solids within the medium, the medium is fed only with: hydrogen; one or more of carbon monoxide and carbon dioxide; a nitrogen source; and any of said nutrients for which the microbial population is not capable of maintaining the amount of the one or more nutrients in the medium within the range relative to the amount of water and total solids within the medium. In a further embodiment at least a portion of at least one of said hydrogen, and said one or more of carbon monoxide and carbon dioxide is provided as part of a gaseous composition comprising any of carbon monoxide, carbon dioxide, hydrogen, nitrogen and one or more hydrocarbons, along with any trace components contained therein.

In one embodiment, the period during which the microbial population is capable of maintaining the amount of the one or more nutrients in the medium within the range relative to the amount of water and total solids within the medium is at least 14 days.

In one embodiment, the period during which the microbial population is capable of maintaining the amount of the one or more nutrients in the medium within the range relative to the amount of water and total solids within the medium is at least 28 days.

In one embodiment, the period during which the microbial population is capable of maintaining the amount of the one or more nutrients in the medium within the range relative to the amount of water and total solids within the medium is at least 48 days.

In one embodiment, the period during which the microbial population is capable of maintaining the amount of the one or more nutrients in the medium within the range relative to the amount of water and total solids within the medium is at least 96 days.

In one embodiment, the period during which the microbial population is capable of maintaining the amount of the one or more nutrients in the medium within the range relative to the amount of water and total solids within the medium is the length of time in which a reactor into which the said medium may be placed is operational.

In one embodiment, the microbial population comprises one or more species of archaea from one of more families comprising: Methanosarcinaceae; Methanosaetaceae; Methanospirillaeae; Methanomicrobiaceae; Methanocorpusculaceae; Methanoregulaceae; Methanobacteriaceae; and Methanococcaceae.

In one embodiment, the microbial population comprises one or more species of bacteria from one or more groups comprising: firmicutes; bacteroidetes; actinobacteria; thermotogae; acidobacteria; spirochaete; synergistetes; chloroflexi; proteobacteria; fibrobacteres; armatimonadetes; fusobacteria; cyanobacteria; tenericutes; and cloacimonetes.

In one embodiment, the pH of the medium is between about 7 and 8.

According to another aspect of the present invention, a method is provided for enriching a population of microbial organisms, comprising: loading a population of microbial organisms into an enrichment vessel, wherein the microbial population comprises: one or more species of hydrogenotrophic methanogens; one or more species of hydrolytic microbes; one or more species of acidogenic microbes, one or more species of acetogenic microbes; and one or more species of acetoclastic microbes; determining the amount of one or more of nutrients, the one or more nutrients comprising: aluminium; boron; calcium; cobalt; copper; iron; potassium; magnesium; manganese; molybdenum; nickel; phosphorus; sulphur; selenium; tungsten; zinc; sodium; nitrogen and vanadium; and if the determined amount of the one or more nutrients is not within a desired range, adjusting the amounts of one or more of nutrients so that the one or more nutrients is present in the enrichment vessel within the desired range, wherein said desired range is as follows: aluminium, wherein the aluminium is present in an amount of at least about 0.01 mg/l; boron, wherein the boron is present in an amount of at least about 0.01 mg/l; calcium, wherein the calcium is present in an amount of at least about 2.0 mg/l; cobalt, wherein the cobalt is present in a range of between about 0.05 mg/l and about 1 mg/l; copper, wherein the copper is present in a range of between about 0.01 mg/l and about 4 mg/l; iron, wherein the iron is present in an amount of at least about 0.5 mg/l; potassium, wherein the potassium is present in an amount of at least about 50 mg/l; magnesium, wherein the magnesium is present in an amount of at least about 20 mg/l; manganese, wherein the manganese is present in a range of about 0.05 mg/l and about 6 mg/l; molybdenum, wherein the molybdenum is present in a range of about 0.05 mg/l and 1.5 mg/l; nickel, wherein the nickel is present in a range of about 0.05 mg/l and 6 mg/l; phosphorus, wherein the phosphorus is present in an amount of at least about 25 mg/l; sulphur, wherein the sulphur is present in an amount of at least about 25 mg/l; selenium, wherein the selenium is present in a range of about 0.05 mg/l and about 1.5 mg/l; sodium, wherein the sodium is present in an amount of at least about 40 mg/l; tungsten, wherein the tungsten is present in a range of about 0.05 mg/l and about 1.5 mg/l; vanadium, wherein the vanadium is present in a range of about 0.03 mg/l and about 1.5 mg/l and zinc, wherein the zinc is present in a range of about 0.03 mg/l and about 9 mg/l.

In one embodiment, the method comprises determining, and if the determined amount is not within a desired range, adjusting the amount of two or more of the nutrients. In one embodiment, the at least two nutrients are sodium and potassium.

In one embodiment, the method comprises determining, and if the determined amount is not within a desired range, adjusting the amount of five or more of the nutrients. In one embodiment, the at least five nutrients are magnesium, calcium, phosphorus, sulphur and iron.

In one embodiment, the method comprises determining, and if the determined amount is not within a desired range, adjusting the amount of nine or more of the nutrients. In one embodiment, the at least nine nutrients are cobalt, copper, manganese, molybdenum, nickel, selenium, tungsten, boron and aluminium.

In one embodiment, the method comprises determining, and if the determined amount is not within a desired range, adjusting the amount of eighteen of the nutrients.

In one embodiment, one or more of biotin, folic acid, riboflavin, thiamine, pyridoxine, nicotinic acid, p-aminobenzoic acid, α-lipoic acid are added to the enrichment vessel.

In one embodiment, during the enrichment the microbial population are fed with one or more of carbon dioxide, carbon monoxide and hydrogen.

In one embodiment, during the enrichment, excess water generated by the microbial population is removed; the amount of the one or more nutrients present in the enrichment vessel is re-determined; and if the re-determined amount of the one or more nutrients is not within a desired range, adjusting the amounts of one or more of nutrients so that the one or more nutrients is present in the enrichment vessel within the desired range.

According to another aspect of the present invention, there is provided the use of a microbial population in a liquid medium to convert carbon dioxide, and hydrogen to methane, wherein: the microbial population comprises: one or more species of hydrogenotrophic methanogens; one or more species of hydrolytic microbes; one or more species of acidogenic microbes, one or more species of acetogenic microbes; and one or more species of acetoclastic microbes; the microbial population is in a medium comprising one or more nutrients comprising at least one of: aluminium, wherein the aluminium is present in an amount of at least about 0.01 mg/l; boron, wherein the boron is present in an amount of at least about 0.01 mg/l; calcium, wherein the calcium is present in an amount of at least about 2.0 mg/l; cobalt, wherein the cobalt is present in a range of between about 0.05 mg/l and about 1 mg/l; copper, wherein the copper is present in a range of between about 0.01 mg/l and about 4 mg/l; iron, wherein the iron is present in an amount of at least about 0.5 mg/l; potassium, wherein the potassium is present in an amount of at least about 50 mg/l; magnesium, wherein the magnesium is present in an amount of at least about 20 mg/l; manganese, wherein the manganese is present in a range of about 0.05 mg/l and about 6 mg/l; molybdenum, wherein the molybdenum is present in a range of about 0.05 mg/l and 1.5 mg/l; nickel, wherein the nickel is present in a range of about 0.05 mg/l and 6 mg/l; phosphorus, wherein the phosphorus is present in an amount of at least about 25 mg/l; sulphur, wherein the sulphur is present in an amount of at least about 25 mg/l; selenium, wherein the selenium is present in a range of about 0.05 mg/l and about 1.5 mg/l; sodium, wherein the sodium is present in an amount of at least about 40 mg/l; tungsten, wherein the tungsten is present in a range of about 0.05 mg/l and about 1.5 mg/l; vanadium, wherein the vanadium is present in a range of about 0.03 mg/l and about 1.5 mg/l and zinc, wherein the zinc is present in a range of about 0.03 mg/l and about 9 mg/l and wherein the microbial population is capable of maintaining the amount of the one or more nutrients in the medium within the range relative to the amount of water and total solids within the medium, without the addition of the one or more nutrients to the medium, for a period of at least 7 days.

In one embodiment, the medium comprises at least two of the nutrients in an amount within the ranges. In one embodiment, the at least two nutrients are sodium and potassium.

In one embodiment, the medium comprises at least five of the nutrients in an amount within the ranges. In one embodiment, the at least five nutrients are magnesium, calcium, phosphorus, sulphur and iron.

In one embodiment, the medium comprises at least nine of the nutrients in an amount within the ranges. In one embodiment, the at least nine nutrients are cobalt, copper, manganese, molybdenum, nickel, selenium, tungsten, boron and aluminium.

In one embodiment, the medium comprises eighteen of the nutrients in an amount within the ranges.

In one embodiment, during the period in which the microbial population is capable of maintaining the amount of the one or more nutrients in the medium within the range relative to the amount of water and total solids within the medium, without the addition of the one or more nutrients to the medium, the medium is fed only with hydrogen; one or more of carbon monoxide and carbon dioxide; and any of said one or more nutrients for which the microbial population is not capable of maintaining the amount of the one or more nutrients in the medium within the range relative to the amount of water and total solids within the medium. In a further embodiment at least a portion of at least one of said hydrogen, and said one or more of carbon monoxide and carbon dioxide is provided as part of a gaseous composition comprising any of carbon monoxide, carbon dioxide, hydrogen, nitrogen and one or more hydrocarbons, along with any trace components contained therein.

In one embodiment, the conversion of carbon dioxide and hydrogen to methane occurs within a reaction vessel, wherein: the reaction vessel comprises at least one inlet to enable carbon dioxide; hydrogen; and a gaseous composition comprising any of carbon monoxide, carbon dioxide, hydrogen, and one or more hydrocarbons, to pass into the reaction vessel; the levels of at least one of methane, carbon dioxide and hydrogen in the gaseous composition are measured; the pH of the medium within the reaction vessel is measured; and the flow of at least one of the gaseous composition, carbon dioxide and hydrogen into the reaction vessel is adjusted in order to maintain at least one desired parameter within the reaction vessel. In a further embodiment, the flow of carbon dioxide into the reaction vessel is adjusted in order to maintain at least one desired parameter within the reaction vessel. In a further embodiment, at least one desired parameter is pH. In a further embodiment, the flow of hydrogen is adjusted in accordance with the level of carbon dioxide measured in the gaseous composition, and in a still further embodiment, the flow of hydrogen is adjusted in order to maintain a ratio of carbon dioxide to hydrogen of between about 18:82 and about 25:75. In a further embodiment, the flow of hydrogen is adjusted in order to maintain a ratio of a combination of carbon monoxide and carbon dioxide to hydrogen of between about 18:82 and about 30:70. In a further embodiment, the flow of hydrogen is adjusted in order to maintain a ratio of carbon monoxide to hydrogen of about 25:75. In a further embodiment, the reaction vessel comprises separate inlets for each of the gaseous composition, carbon dioxide and hydrogen.

In one embodiment, during a period of the conversion of carbon dioxide and hydrogen to methane within a reaction vessel, there is no addition of microbes to the reaction vessel during the period of at least seven days. In a further embodiment, the period is at least 14 days. In a further embodiment, the period is at least 28 days. In a further embodiment, the period is at least 48 days. In a further embodiment, the period is at least 96 days. In a further embodiment, the period is the length of time in which a reactor into which the said medium may be placed is operational.

In one embodiment, the microbial population comprises one or more species of archaea from one of more families comprising: Methanosarcinaceae; Methanosaetaceae; Methanospirillaeae; Methanomicrobiaceae; Methanocorpusculaceae; Methanoregulaceae; Methanobacteriaceae; and Methanococcaceae.

In one embodiment, the microbial population comprises one or more species of bacteria from one or more groups comprising: firmicutes; bacteroidetes; actinobacteria; thermotogae; acidobacteria; spirochaete; synergistetes; chloroflexi; proteobacteria; fibrobacteres; armatimonadetes; fusobacteria; cyanobacteria; tenericutes; and cloacimonetes.

In one embodiment, wherein the liquid within the reaction vessel is circulated by means of a pump, wherein the pump mixes the one or more gases entering the reaction vessel with the liquid, so as to form bubbles with an average diameter of less than about 1 mm. In some embodiments, the bubbles have an average diameter of less than about 800 µm. In some embodiments, the bubbles have an average diameter of less than about 600 µm. In some embodiments, the bubbles have an average diameter of less than about 400 µm. In some embodiments, the bubbles have an average diameter of less than about 200 µm. In a further embodiment, the inlet of the pump is proximal to one or more inlets into said reaction vessel for any of: carbon dioxide; hydrogen; and a gaseous composition comprising any of carbon monoxide, carbon dioxide, hydrogen, nitrogen and one or more hydrocarbons. In a further embodiment, said pump is a centrifugal pump.

In one embodiment, the level of liquid in the reaction vessel is monitored, and wherein excess water is removed once the amount of liquid in the reaction vessel reaches or exceeds a predetermined level. In some embodiments, the removal of excess water is achieved without removing nutrients and microbes from the liquid medium. In some embodiments, the removal of excess water is achieved without removing nutrients and microbes from the reaction vessel. In some embodiments, the removal of excess water is via evaporation. In some embodiments the removal of excess water is via osmosis. In further embodiments, the removal of excess water comprises the use of any of: a fan; suction device; or blowing device, for withdrawing gas from the headspace of the reaction vessel, passing the gas through a condensing or desiccating unit, and returning the gas to the headspace in the reaction vessel. In another further embodiment, the removal of excess water comprises the use of a container comprising a solution with a solute, e.g. a salt, such as for example sodium chloride, concentration of greater osmotic potential than that of the liquid medium, the container being attached to the reaction vessel by a port comprising an osmosis membrane with a pore size of less than 5 angstroms, wherein the solute concentration is adjusted to control the degree to which water moves from the reaction vessel into the container. In another further embodiment, the removal of excess water comprises the use of a filtration device comprising a series of filters of decreasing pore size, the filtration device being connected to a port on the reaction vessel, wherein a pump is utilised to drive the liquid through said filtration device towards a tank; in some further embodiments, the filters comprise one or more of a particle filter, a micro-filter, an ultra-filter, a nano-filter and a filter permitting reverse osmosis; in further embodiments, the pump is a reversible pump.

In one embodiment, the efficiency of conversion of carbon dioxide to methane is at least 95%.

In one embodiment, the efficiency of conversion of carbon dioxide to methane is at least 99.7%.

In one embodiment, there is an output of methane of at least 1.9 litres of methane per gram of volatile solids per day In one embodiment, there is an output of methane of at least 3.2 litres of methane per gram of volatile solids per day.

In one embodiment, there is a conversion of 120 litres of hydrogen and carbon dioxide per litre of microbial culture per day into at least about 24.2 litres of methane per litre of microbial culture per day.

In one embodiment, two reaction vessels are joined in series and there is a conversion of 200 litres of hydrogen and carbon dioxide per litre of microbial culture per day into 40.65 litres of methane per litre of microbial culture per day.

In one embodiment, the pH of said liquid medium is between about 7 and 8.

In another aspect of the invention, there is provided a system for converting carbon dioxide and hydrogen to methane, wherein the system comprises a reaction vessel comprising a microbial population in a liquid medium, wherein the microbial population comprises: one or more species of hydrogenotrophic methanogens; one or more species of hydrolytic microbes; one or more species of acidogenic microbes, one or more species of acetogenic microbes; and one or more species of acetoclastic microbes; the medium comprising one or more nutrients comprising at least one of: aluminium, wherein the aluminium is present in an amount of at least about 0.01 mg/l; boron, wherein the boron is present in an amount of at least about 0.01 mg/l; calcium, wherein the calcium is present in an amount of at least about 2.0 mg/l; cobalt, wherein the cobalt is present in a range of between about 0.05 mg/l and about 1 mg/l; copper, wherein the copper is present in a range of between about 0.01 mg/l and about 4 mg/l; iron, wherein the iron is present in an amount of at least about 0.5 mg/l; potassium, wherein the potassium is present in an amount of at least about 50 mg/l; magnesium, wherein the magnesium is present in an amount of at least about 20 mg/l; manganese, wherein the manganese is present in a range of about 0.05 mg/l and about 6 mg/l; molybdenum, wherein the molybdenum is present in a range of about 0.05 mg/l and 1.5 mg/l; nickel, wherein the nickel is present in a range of about 0.05 mg/l and 6 mg/l; phosphorus, wherein the phosphorus is present in an amount of at least about 25 mg/l; sulphur, wherein the sulphur is present in an amount of at least about 25 mg/l; selenium, wherein the selenium is present in a range of about 0.05 mg/l and about 1.5 mg/l; sodium, wherein the sodium is present in an amount of at least about 40 mg/l; tungsten, wherein the tungsten is present in a range of about 0.05 mg/l and about 1.5 mg/l; vanadium, wherein the vanadium is present in a range of about 0.03 mg/l and about 1.5 mg/l and zinc, wherein the zinc is present in a range of about 0.03 mg/l and about 9 mg/l and wherein the microbial population is capable of maintaining the amount of the one or more nutrients in the medium within the range relative to the amount of water and total solids within the medium, without the addition of the one or more nutrients to the medium, for a period of at least 7 days.

In one embodiment, the medium comprises at least two of the nutrients in an amount within the ranges. In one embodiment, the at least two nutrients are sodium and potassium.

In one embodiment, the medium comprises at least five of the nutrients in an amount within the ranges. In one embodiment, the at least five nutrients are magnesium, calcium, phosphorus, sulphur and iron.

In one embodiment, the medium comprises at least nine of the nutrients in an amount within the ranges. In one embodiment, the at least nine nutrients are cobalt, copper, manganese, molybdenum, nickel, selenium, tungsten, boron and aluminium.

In one embodiment, the medium comprises eighteen of the nutrients in an amount within the ranges.

In one embodiment, during the period the medium is fed only with: hydrogen; one or more of carbon monoxide and carbon dioxide; and any of the one or more nutrients not present in the ranges.

In one embodiment, the reaction vessel comprises an inlet for a gaseous composition comprising any of carbon monoxide, carbon dioxide, hydrogen, and one or more hydrocarbons, along with any trace components contained therein.

In one embodiment, the conversion of carbon dioxide and hydrogen to methane occurs within the reaction vessel, wherein: the reaction vessel comprises at least one inlet to enable carbon dioxide; hydrogen; and a gaseous composition comprising any of carbon monoxide, carbon dioxide, hydrogen, and one or more hydrocarbons, to pass into the reaction vessel; the system comprises sensors for measuring the levels of at least one of methane, carbon dioxide and hydrogen in the gaseous composition; and a control system for adjusting the flow of at least one of the gaseous composition, carbon dioxide and hydrogen into the reaction vessel in order to maintain at least one desired parameter within the reaction vessel. In a further embodiment, the control system is capable of adjusting the flow of carbon dioxide into the reaction vessel in order to maintain at least one desired parameter within the reaction vessel. In a further embodiment, at least one desired parameter is the pH of the liquid medium within the reaction vessel. In a further embodiment, the control system is capable of adjusting the flow of hydrogen in accordance with the level of carbon dioxide measured in the gaseous composition. In a further embodiment, the control system is capable of adjusting the flow of hydrogen in order to maintain a ratio of carbon dioxide to hydrogen of between about 18:82 and about 25:75. In a further embodiment, the flow of hydrogen is adjusted in order to maintain a ratio of a combination of carbon monoxide and carbon dioxide to hydrogen of between about 18:82 and about 30:70. In a further embodiment, the flow of hydrogen is adjusted in order to maintain a ratio of carbon monoxide to hydrogen of about 25:75.

In one embodiment, the reaction vessel comprises separate inlets for each of the gaseous composition, carbon dioxide and hydrogen.

In one embodiment, the microbial population comprises one or more species of archaea from one or more families comprising: Methanosarcinaceae; Methanosaetaceae; Methanospirillaeae; Methanomicrobiaceae; Methanocorpusculaceae; Methanoregulaceae; Methanobacteriaceae; and Methanococcaceae.

In one embodiment, the microbial population comprises one or more species of bacteria from one or more groups comprising: firmicutes; bacteroidetes; actinobacteria; thermotogae; acidobacteria; spirochaete; synergistetes; chloroflexi; proteobacteria; fibrobacteres; armatimonadetes; fusobacteria; cyanobacteria; tenericutes; and cloacimonetes.

In one embodiment, the liquid within the reaction vessel is circulated by means of a pump, wherein the pump mixes the one or more gases entering the reaction vessel with the liquid, so as to form bubbles with an average diameter of less than about 1 mm. In some embodiments, the bubbles have an average diameter of less than about 800 µm. In some embodiments, the bubbles have an average diameter of less than about 600 µm. In some embodiments, the bubbles have an average diameter of less than about 400 µm. In some embodiments, the bubbles have an average diameter of less than about 200 µm. In one embodiment, the system comprises at least one sensor capable of monitoring the level of liquid in the reaction vessel, and means for removing excess water once the amount of liquid in the reaction vessel reaches or exceeds a predetermined level. In a further embodiment, the means for removing excess water excess can remove water from the reaction vessel without removing the nutrients or the microbes from the liquid medium. In some embodiments, the means for removing excess water excess can remove water from the reaction vessel without removing the nutrients or the microbes from the reaction vessel. In some embodiments, the means for removing excess water comprises osmosis and/or evaporation. In a further embodiment, the means for removing excess water comprises a fan or a suction or a blowing device for withdrawing gas from the headspace of the reaction vessel, passing the gas through a condensing or desiccating unit, and returning the gas to the headspace in the reaction vessel. In another further embodiment, the means for removing excess water comprises a container comprising a solution with solute concentration of greater osmotic potential than that of the liquid medium, the container being attached to the reaction vessel by a port comprising an osmosis membrane with a pore size of less than 5 angstroms, wherein the solute concentration is capable of being adjusted to control the degree to which water moves from the reaction vessel into the container. In another further embodiment, the means for removing excess water comprises a filtration device comprising a series of filters of decreasing pore size, the filtration device being connected to a port on the reaction vessel, wherein the system comprises a pump capable of driving the liquid through the filtration device towards a tank. In a further embodiment, the filters comprise one or more of a particle filter, a micro-filter, an ultra-filter, a nano-filter and a filter permitting reverse osmosis. In a further embodiment, the pump is a reversible pump.

In one embodiment, the efficiency of conversion of carbon dioxide to methane with the system is at least 95%.

In one embodiment, the efficiency of conversion of carbon dioxide to methane with the system is at least 99.7%.

In one embodiment, there is an output of methane from the system of at least 9 litres of methane per gram of volatile solids per day.

In one embodiment, there is an output of methane from the system of at least 3.2 litres of methane per gram of volatile solids per day.

In one embodiment, there is a conversion of 120 litres of hydrogen and carbon dioxide per litre of microbial culture per day into at least about 24.2 litres of methane per litre of microbial culture per day.

In one embodiment, two reaction vessels are joined in series and there is a conversion of 200 litres of hydrogen and carbon dioxide per litre of microbial culture per day into 40.65 litres of methane per litre of microbial culture per day.

In one embodiment, the pH of the liquid medium is between about 7 and 8.

Further features and advantages of the invention will become apparent from the following description of preferred embodiments of the invention, given by way of example only, which is made with reference to the accompanying drawings.

BRIEF DESCRIPTION OF THE DRAWINGS

FIG. 11 shows a table setting out the concentration of 16 elements inside the same reaction vessel at three different dates.

FIG. 12 shows the suggested minimal concentrations of 19 nutrients.

DETAILED DESCRIPTION OF CERTAIN INVENTIVE EMBODIMENTS

Figure 1:
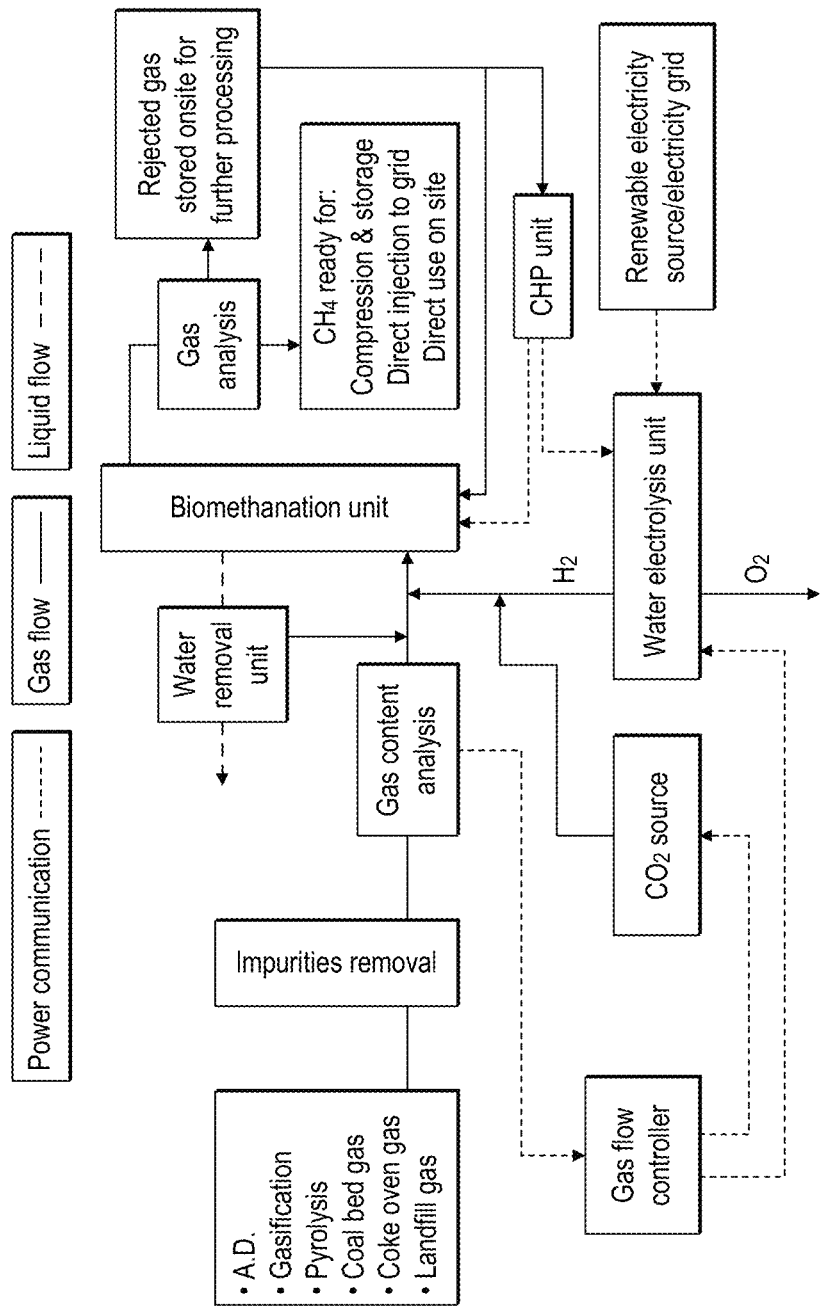
FIG. 1 shows an example of a system in which the concentration of methane within a biogas or a contaminated gas may be increased.

The present invention provides methods and apparatus for the conversion of carbon dioxide, carbon monoxide and hydrogen into methane using microbial biocatalysis. The conversion is carried out by an enriched culture of hydrogenotrophic archaea in combination with further microbial populations comprising hydrolytic, acidogenic, acetogenic and acetoclastic populations. The medium in which the microbial populations are maintained is adjusted so that after enrichment has occurred, a self-sustaining culture is obtained. The methods and apparatus of the invention can be utilised in order to upgrade a variety of gases including but not limited to: biogas from anaerobic digestion plants; gasification/pyrolysis gas; coal bed gas; coke oven gas; and landfill gas. The methods and apparatus of the invention can be utilised as a system for the conversion of electricity to methane gas. As such, the apparatus can be incorporated into a complete energy storage system for renewable energy generation plants that suffer from intermittency of generation. Methane can then be used as a chemical or as an energy source, e.g. for combustion in order to produce heat, as a transport fuel or for electricity generation. The use of a self-sustaining culture can provide significant efficiencies over known biomethanation systems.

In addition to the carbon source several nutrients play an important role as growth and metabolism factors for the microbial population. In previously known systems, these are added to the inoculum in the form of synthetic media. When a pure culture of hydrogenotrophic methanogens is used, a nutrient solution is essential for growth but also for the maintenance of a dense and healthy microbial population. Dead cells need to be removed in order to be able to replenish the culture so as to maintain a high biomass density, preserving the efficiency of the system; however, this unavoidably results to the removal of nutrients. Repeated nutrient addition is therefore the only option as far as pure cultures are concerned, which adds considerably to the overall running costs of the system, as well as being an environmental burden. This inefficiency is reduced, and potentially removed, by the use of a self-sustaining culture. This is provided by the present invention via the provision of a mixed microbial population in combination with a medium in which the concentration of one or more nutrients have been adjusted to an optimum level.

It has been discovered that even in microbial populations which are composed of substantially hydrogenotrophic methanogens, it is advantageous to include populations of one or more species of hydrolytic microbes; one or more species of acidogenic microbes; and one or more species of acetogenic microbes. Although the presence of such microbes reduces the biomass of hydrogenotrophic methanogens relative to the overall biomass, the presence of these additional microbes facilitates in the degradation of dead microbial cells. The hydrogen, carbon dioxide and organic acids produced by the acidogenic and acetogenic cells are utilised by the hydrogenotrophic methanogens. As the acetogenic microbes produce acetate, one or more species of acetoclastic microbes should also be included. Because these additional microbes enable the degradation of dead microbial cells, there is no need to remove dead cells, even in populations comprising substantially hydrogenotrophic methanogens, or in populations comprising substantially entirely hydrogenotrophic methanogens.

The primary products from the cellular degradation are ultimately converted to methane. Further, nutrients within the cells are released back into the medium whereby they can be reutilised by the microbial population. Consequently, provided the concentration of a particular nutrient within a medium is adjusted to an optimum level, the recycling of these nutrients by the microbial population shall mean that no further nutrients need to be added for an extended period, and potentially indefinitely. Nutrients to which this applies comprise: aluminium; boron; calcium; cobalt; copper; iron; potassium; magnesium; manganese; molybdenum; nickel; phosphorus; sodium; sulphur; selenium; tungsten; vanadium and zinc. Hence, for those one or more nutrients, which are present at an optimum level within the medium, there is no need to make further additions of such one or more nutrients for an extended period. The extended period may be at least 7, 14, 28, 48, or 96 days, the length of time in which a reactor into which the said medium may be placed is operational, or indefinitely.

The retention of nutrients within the reaction system is seen in FIG. 11. FIG. 12 shows the suggested minimum amounts which should be contained in the medium. Nitrogen is also listed here, as the levels for nitrogen may be adjusted at the same time as the other nutrients. However, nitrogen within the medium can volatilise to the output gas and leave the reaction vessel; it may therefore be necessary to add additional nitrogen when values drop. This may be done, for example, by adding ammonia or ammonium salts in aqueous solution.

The optimum levels for each nutrient within the medium will vary but in each case is within the following limits: aluminium, wherein the aluminium is present in an amount of at least about 0.01 mg/l; boron, wherein the boron is present in an amount of at least about 0.01 mg/l; calcium, wherein the calcium is present in an amount of at least about 2.0 mg/l; cobalt, wherein the cobalt is present in a range of between about 0.05 mg/l and about 1 mg/l; copper, wherein the copper is present in a range of between about 0.01 mg/l and about 4 mg/l; iron, wherein the iron is present in an amount of at least about 0.5 mg/l; potassium, wherein the potassium is present in an amount of at least about 50 mg/l; magnesium, wherein the magnesium is present in an amount of at least about 20 mg/l; manganese, wherein the manganese is present in a range of about 0.05 mg/l and about 6 mg/l; molybdenum, wherein the molybdenum is present in a range of about 0.05 mg/l and 1.5 mg/l; nickel, wherein the nickel is present in a range of about 0.05 mg/l and 6 mg/l; phosphorus, wherein the phosphorus is present in an amount of at least about 25 mg/l; sulphur, wherein the sulphur is present in an amount of at least about 25 mg/l; selenium, wherein the selenium is present in a range of about 0.05 mg/l and about 1.5 mg/l; sodium, wherein the sodium is present in an amount of at least about 40 mg/l; tungsten, wherein the tungsten is present in a range of about 0.05 mg/l and about 1.5 mg/l; vanadium, wherein the vanadium is present in a range of about 0.03 mg/l and about 1.5 mg/l and zinc, wherein the zinc is present in a range of about 0.03 mg/l and about 9 mg/l. Unless there are high levels of halophiles within the microbial population, the amounts of sodium, potassium and calcium should not be above 2.5 g/l. FIG. 12 also sets out examples of compounds which may be added to adjust the amount of a particular nutrient.

Efficiency and reduced running costs can be achieved by optimising the level of one nutrient within the system, with greater efficiencies being achieved as more nutrients are optimised. With the media in which all eighteen cited nutrients have been optimised, the medium need only be fed with carbon monoxide and/or carbon dioxide and hydrogen and a topped up nitrogen (for example ammonia or ammonium salts in aqueous solution) to make up any losses due to volatilisation to the output gas. In some embodiments, one or more of the carbon monoxide and/or carbon dioxide and hydrogen and nitrogen are provided as a gaseous composition, for example a biogas, which may also contain other hydrocarbons and trace components (i.e. impurities). In some embodiments, the medium may be fed with a gaseous composition and may be additionally fed with any of carbon dioxide and hydrogen, to enable the amounts being fed to the medium to be adjusted, dependent upon the quantities present in the gaseous composition. In embodiments in which some of the eighteen cited nutrients have been not been optimised, the medium may be additionally fed with these nutrients.

A range of different hydrogenotrophic archaea may be used in the present invention, including, for example, one or more species of archaea from the orders comprising: methanosarcinales; methanomicrobiales; methanobacteriales; and methanococcales. In particular, one or more species of archaea may be used in the present invention from within families comprising: Methanosarcinaceae; Methanospirillaeae; Methanomicrobiaceae; Methanocorpusculaceae; Methanoregulaceae; Methanobacteriaceae; and Methanococcaceae. Species of archaea within these families, which may be used in the present invention comprise: *Methanosarcina* sp.; *Methanosarcina mazei*; *Methanosarcina thermophila*; *Methanosarcina barkeri*; *Methanosarcina acetivorans*; *Methanosarcina semesiae*; *Methanosarcina siciliae*; *Methanosarcina vacuolata*; *Methanomethylovorans hollandica*; *Methanospirillum* sp.; *Methanospirillum lacunae*; *Methanospirillum hungatei*; *Methanoculleus* sp.; *Methanoculleus bourgensis*; *Methanoculleus chikugoensis*; *Methanoculleus palmolei*; *Methanoculleus olentangyi*; *Methanoculleus submarinus*; *Methanoculleus marisnigri*; *Methanoculleus thermophilicum*; *Methanoculleus oldenburgensis*; *Methanogenium boonei*; *Methanomicrobium mobile*; *Methanofollis tationis*; *Methanofollis aquemaris*; *Methanofollis liminatans*; *Methanocorpusculum* sp.; *Methanocorpusculum parvum*; *Methanocorpusculum sinense*; *Methanocorpusculum bavaricum*; *Methanocorpusculum aggregans*; *Methanocorpusculum labreanum*; *Methanolinea tarda*; *Methanobacterium* sp.; *Methanobacterium kanagiense*; *Methanobacterium alcaliphilum*; *Methanobacterium bryantii*; *Methanobacterium espanolae*; *Methanobacterium subterraneum*; *Methanobacterium defluvii*; *Methanobacterium thermoformicicum*; *Methanobacterium thermoaggregans*; *Methanobacterium oryzae*; *Methanobacterium palustre*; *Methanobacterium thermoflexum*; *Methanobacterium ivanovii*; *Methanobacterium formicicum*; *Methanobrevibacter smithii*; *Methanobrevibacter cuticularis*; *Methanobrevibacter ruminantium*; *Methanobrevibacter filiformis*; *Methanobrevibacter arboriphilus*; *Methanobrevibacter curvatus*; *Methanothermobacter thermoautotrophicus*; *Methanothermobacter wolfeii*; *Methanothermobacter marburgensis*; *Methanococcus vannielii*; *Methanococcus deltae*; *Methanococcus aeolicus*; and *Methanococcus voltae*.

The one or more species of archaea may also comprise one or more as yet unclassified archaea comprising: *Methanomassiliicoccus luminyensis* strain B10; uncultured methanogenic archaeon clone mera_HANU82; uncultured *Methanosarcina* sp. clone KM95; uncultured archaeon clone mcrA_dig_E17; uncultured archaeon clone ATB-EN-6450-M102; uncultured archaeon clone asg_m_388M-C; uncultured archaeon clone mcrA_dig_DC17; uncultured archaeon clone 7A86d393bp-47; uncultured archaeon clone mcrA_dig_E1; and uncultured archaeon clone Contig_34.

Further, *Methanosaeta* sp.; *Methanosaeta concilii*; *Methanosaeta thermophila*; *Methanosaeta harundinacea* and a range of different hydrolytic, acidogenic and acetogenic bacteria may be used including, for example, one or more species of bacteria from the groups comprising: firmicutes; bacteroidetes; actinobacteria; thermotogae; acidobacteria; spirochaetes; synergistetes; chloroflexi; proteobacteria; fibrobacteres; armatimonadetes; fusobacteria; cyanobacteria; tenericutes; and cloacimonetes.

A microbial population for use in the present invention may be produced by taking a pre-existing microbial population comprising one or more species of hydrogenotrophic methanogens; one or more species of hydrolytic microbes; one or more species of acidogenic microbes, one or more species of acetogenic microbes; and one or more species of acetoclastic microbes, and performing an enriching step to increase the concentration of hydrogenotrophic methanogens relative to the concentration of other microbes. The enrichment step is performed to a degree sufficient to produce a microbial population with a greatly increased concentration of hydrogenotrophic methanogens relative to the other microbes, whilst still retaining one or more species of hydrolytic microbes; one or more species of acidogenic microbes, one or more species of acetogenic microbes; and one or more species of acetoclastic microbes within the microbial population. The hydrogenotrophic activity of the enriched population is increased significantly. For example, an initial inoculum may be required to have at least $10^2$ per ml of detectable cells for at least one group of hydrogenotrophic methanogens. As an example, the inoculum as received (prior to enrichment) may have specific methanogenic activities for hydrogen and carbon dioxide conversions as low as 0.06 l methane/g VS per day with only 3% of methane measured at the output being achieved when operating the apparatus on continuous basis, whilst the enriched hydrogenotrophic culture may achieve 99.7% methane at the outflow and with specific yield above 1.9 l methane/g VS per day.

The initial microbial population prior to enrichment may be obtained by taking a sample of a microbial population present in an existing anaerobic digestion system, for example a system used to break down sewage or other organic matter. Such anaerobic digestion systems typically contain one or more species of each of acetoclastic and hydrogenotrophic methanogens and one or more species of hydrolytic microbes; one or more species of acidogenic microbes, and one or more species of acetogenic microbes.

The enrichment process may proceed by placing a pre-existing sample of a microbial population into an enrichment vessel, for example by adding a microbial inoculum to a liquid medium. Preferably the sample is stored for no more than one, two, five or ten days prior to enrichment. In general, the sample will be sieved to remove larger particles (e.g. grit, sand, unwanted organic matter) from the sample prior to being placed in the enrichment vessel. In one embodiment, a sieve with a mesh size of 200, 400, 600 or 800 microns may be used. In certain embodiments, the total solid content placed into the enrichment vessel may be below 3% w/w; below 2% w/w, or approximately 1% w/w. Alternatively, the initial sample for enrichment may be created for the purposes of being enriched.

At this stage an analysis of particular nutrients may be performed for example for aluminium, boron, calcium, cobalt, copper, iron, potassium, sodium, magnesium, manganese, molybdenum, nickel, phosphorus, selenium, sulphur, tungsten, vanadium, zinc, as well as total nitrogen. If necessary, these values can be corrected accordingly by dilution or by addition of a nutrient solution. This correction may be to ensure adequate provision of nutrients during enrichment. In some embodiments, the amounts of the nutrients may be adjusted in order provide an optimum level of the nutrients, as set out above. If a significant excess of any of these elements is likely to create inhibition of enrichment, then an initial dilution of the medium in which the microbial populations is required. In some embodiments, one or more vitamins, for example biotin, folic acid, riboflavin, thiamine, pyridoxine, nicotinic acid, p-aminobenzoic acid, α-lipoic acid, pantothenic acid, and B12 may also be added to aid with metabolic activity.

Enrichment takes place inside an enrichment vessel (which may or may not be a hydrogenotrophic biomethanation reactor vessel) and under optimum physicochemical conditions, comprising: temperature; pressure; pH; redox potential; light wavelength allowed to reach the microbes; total solids and volatile solids concentration; nutrient concentration; composition of feeding gas; liquid recirculation flow; and method of liquid recirculation. These conditions are selected for optimum growth of hydrogenotrophic populations. Providing a substrate only of hydrogen, carbon monoxide and carbon dioxide will result in microbial enhancement of the microbes, which use these substrates as feedstocks. Other microbes will only support the conversion of decayed microbial biomass. For example, by feeding only with carbon dioxide and hydrogen the food for all other microbes is limited such that they must rely on dead cells as the only source of organic matter. Temperature, redox, pH and nutrients are also adjusted to favour hydrogenotrophs. All other populations will consequently be adjusted to function as a support background for hydrogenotrophs. In general, the temperature used should be in the optimum range of the operating temperature of the source of the microbial population being enriched, although this may be increased for example where thermophilic operation or decreased where psychrophilic operation is desired. During enrichment, the enrichment vessel may be fed with hydrogen, carbon monoxide and carbon dioxide, with the flowrate controlled based on the pH of the medium, as well as conversion efficiency as discussed below. As the microbial population, and in particular the population of hydrogenotrophic methanogens, increases, the flow rate of carbon dioxide and hydrogen will need to be increased.

Excess water generated during the enrichment process may be discharged and the nutrient levels adjusted accordingly. Alternatively, a system of dewatering in which excess water is removed without the removal of nutrients, as set out below, may be used so as to avoid the need for nutrient adjustment.

The enrichment period is determined by the grams of biomass per litre needed to be achieved and related activity. The doubling times of hydrogenotrophic populations have been reported to be in the range of hours, generally 4-12 hours, and therefore the enrichment period is typically in the range of 8 to 20 days.

The enriched culture can be utilised as collected from the enrichment vessel or separated by a membrane filter or centrifugation and concentrated for ease of transportation. Enriched cultures may have at least 5 g of volatile solids (VS) per litre. In some embodiments, the enriched culture will have about 10 g of volatile solids per litre. In some embodiments, the enriched culture will have about 20 g of volatile solids per litre. "Volatile solids" refers to the amount of organic matter within the reaction vessel. After enrichment, the only organic matter will be the microbial biomass, i.e. the live and dead microbial cells.

The enrichment process may in particular enrich for archaea falling within the orders of methanosarcinales, methanomicrobiales, methanobacteriales and methanococcales.

The enriched population of microbes may be used to convert hydrogen and carbon dioxide to methane, according to the overall reaction:

$$4H_2 + CO_2 \rightarrow CH_4 + 2H_2O$$

The enriched population may also be used to convert carbon monoxide to carbon dioxide or acetic acid for subsequent processing to methane or convert directly to methane, according to the overall reactions:

$$CO + H_2O \rightarrow H_2 + CO_2$$

$$4CO + 2H_2O \rightarrow CH_4 + 3CO_2$$

$$4CO + 2H_2O \rightarrow CH_3COOH + 2CO_2$$

$$CO + 3H_2 \rightarrow CH_4 + H_2O$$

There are bacterial and archaeal microorganisms (e.g. *Rhodospirillum rubrum, Rubrivivax gelatinosus, Carboxydothermus hydrogenoformans, Moorella thermoacetica, Acetobacterium woodii, Methanosarcina barkeri, Methanothermobacter thermoautotrophicus* and *Methanosarcina acetivorans*), which can facilitate the conversion of carbon monoxide and which may form part of the microbial population.

The enriched population of microbes may be placed into a reaction vessel, for example as part of a complete medium, or as an inoculum introduced into a pre-existing medium. In some embodiments, the microbial population will be attached on a solid substrate and then introduced into the liquid medium. In some embodiments the enrichment vessel will be the reaction vessel.

The enrichment process may increase the ability of the microbial population to produce methane from hydrogen and carbon dioxide by about a 25 to 45-fold increase, and potentially a 28 to 35 fold increase, and potentially a 30 to 32 fold increase, all measured on the basis of litres of methane produced per gram of volatile solids per day.

After the initial introduction of the enriched microbial culture into the reaction vessel, the biomethanation process has no further need of microbial supplementation for at least 7, 14, 28, 48 or 96 days, or at all.

The microbial culture will maintain conversion activity (i.e. will be able to continue without microbial or nutrient supplementation, as previously) after a restart of gas feeding even after a period of no gas feeding; periods for which no gas is fed can be for 24 hours, 2 days, 7 days and 30 days. Following the restart of gas feeding, the period during which the microbial population is capable of maintaining the amount of the one or more nutrients in the medium within the range relative to the amount of water and total solids within the medium is at least 7, 14, 28, 48 or 96 days, or as long as the reactor is operational.

The reaction vessel will comprise at least one inlet to enable the feeding of the medium with hydrogen, and at least one of carbon monoxide and carbon dioxide. An inlet may also be used to provide any of aluminium, boron, calcium, cobalt, copper, iron, potassium, magnesium, manganese, molybdenum, nickel, phosphorus, selenium, sulphur, tungsten, sodium, vanadium, nitrogen and zinc, for which the amounts have not been optimised. In some embodiments at least a portion of at least one of said hydrogen, and one or more of carbon monoxide and carbon dioxide is provided as part of a gaseous composition comprising any of carbon monoxide, carbon dioxide, hydrogen, and one or more hydrocarbons, along with any trace components (i.e. impurities) contained therein. The gaseous composition may be for example a biogas, and may be obtained from any suitable source, for example from plants conducting the anaerobic digestion of carbonaceous material, gasification and/or pyrolysis plants, coal bed gas, coke oven gas and landfill gas. Where a gaseous composition comprising any of carbon monoxide, carbon dioxide, hydrogen, nitrogen and one or more hydrocarbons, along with any trace components (i.e. impurities), such as a biogas, is being fed to the medium, the gas might need to be stripped of significant impurities (e.g. any of hydrogen sulphide, nitrogen, oxygen, ammonia, siloxanes, hydrocarbons, and water) before entering the reaction vessel.

In some embodiments, the reaction vessel will comprise multiple inlets, for example separate inlets for hydrogen and carbon dioxide. In some embodiments, there will be a separate inlet for the gaseous composition, e.g. the biogas, in addition to separate inlets for carbon dioxide and hydrogen.

Where a gaseous composition, for example a biogas, is being fed to the medium, the levels of at least one of methane, carbon dioxide and hydrogen in said gaseous composition are measured. In some embodiments, the levels of at least carbon dioxide and hydrogen in the gaseous composition are measured. By measuring the amount of carbon dioxide in the gaseous composition, an assessment can be made as to whether more or less carbon dioxide should be added to the reaction vessel. If less carbon dioxide is needed, the flow of the gaseous composition can be slowed or stopped. If more carbon dioxide is needed, additional carbon dioxide can be provided, for example via a second inlet. Adjusting the amount of carbon dioxide can be used not only to ensure sufficient substrate is available for the microbial population, but also to control the pH of the medium. The reactions of carbon dioxide in water are as follows:

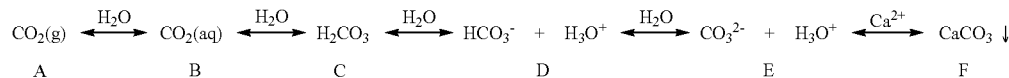

The equilibrium between these phases depends mainly on the amount of available carbon dioxide. In order for the microbes to utilise the carbon dioxide, it must be present in its aqueous phase (B). When the rate of injection into the liquid medium exceeds the rate of utilisation, a portion of the carbon dioxide gets converted to carbonic acid (C), which is a weak acid and dissociates in two steps (D) to give hydrogen carbonate and (E) to give carbonate. In the absence of stronger bases this lowers the pH of the solution. Furthermore, if free cations are present in the solution they will interact with the carbonate anions, and may form insoluble salts such as calcium carbonate and magnesium carbonate (F).

Figure 9:
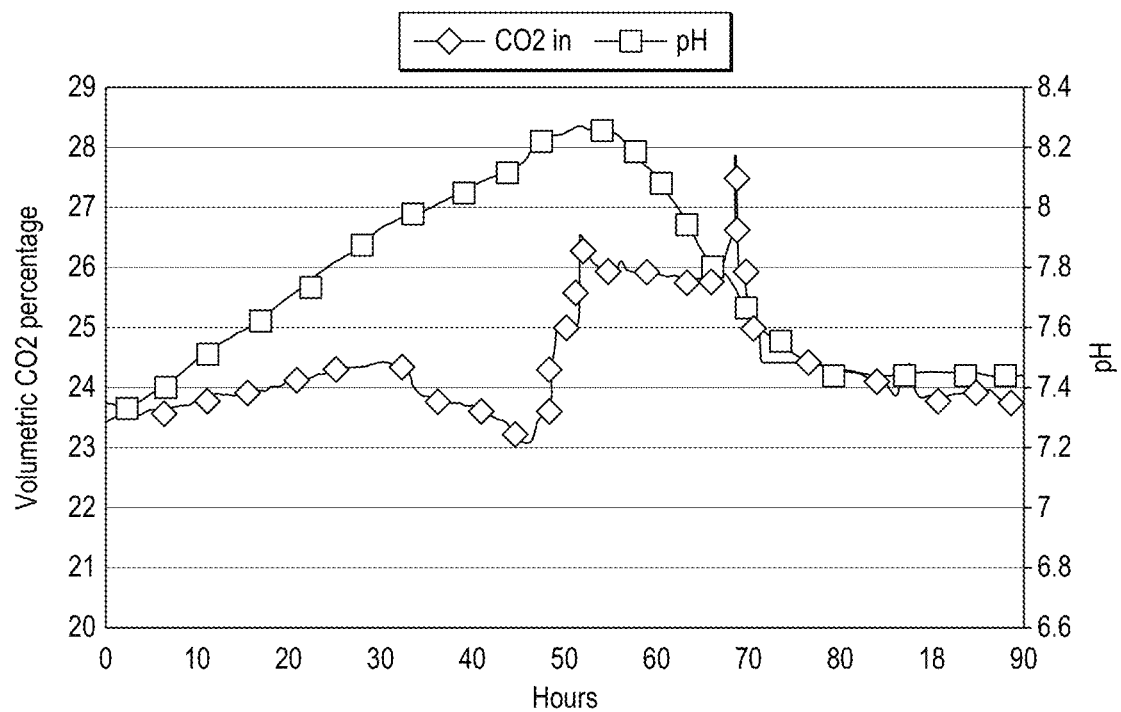
FIG. 9 shows a chart demonstrating how pH is affected by the volumetric percentage of carbon dioxide entering the reaction vessel.

FIG. 9 shows how pH is affected by the volumetric percentage of carbon dioxide entering the reaction vessel. From 0 to 40 hours, carbon dioxide is maintained at slightly lower levels than required. During this period, biological conversion of carbon dioxide to methane occurs at a higher rate than the rate of conversion of carbon dioxide to hydrogen carbonate.

Figure 10:
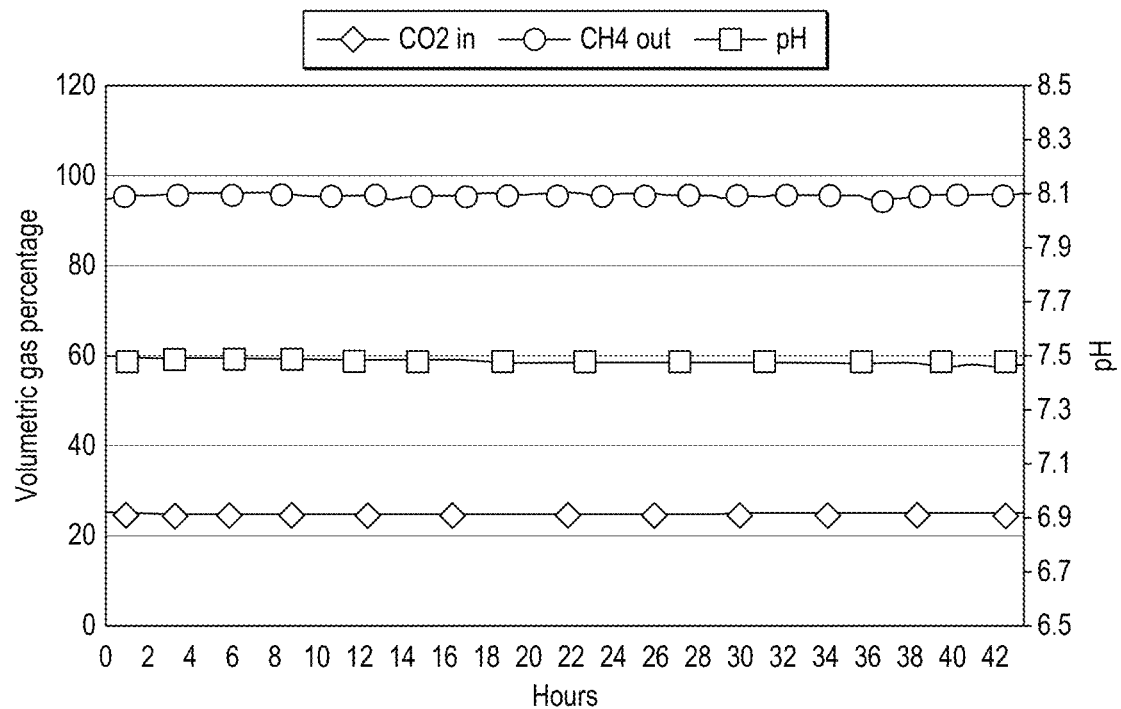
FIG. 10 shows a chart which depicts the input of carbon dioxide, the continuous high output of methane and control of the pH of a reaction system.

Although the stoichiometry of the biological conversion of carbon dioxide to methane requires a ratio of 20% carbon dioxide to 80% hydrogen, an extra amount of carbon dioxide is needed to maintain the formation of the right amount of carbonic acid so that pH is kept at optimum levels, typically between about 7.0-7.8 pH, which is normally stated as optimal for growth and metabolism of hydrogenotrophic populations. Consequently, the flow of hydrogen into the reaction vessel, for example via a separate inlet, may be adjusted in accordance with the level of carbon dioxide measured in said gaseous composition, and may potentially be adjusted to take into account any carbon dioxide introduced into the reaction vessel in addition to that contained in the gaseous composition. For example, the flow of hydrogen is adjusted in order to maintain a ratio of carbon dioxide to hydrogen of between about 18:82 and about 25:75. According to the experimental data, the optimum carbon dioxide to hydrogen ratio for a reactor running at steady state, has been found to be 22:78-24:76. This is apparent in FIG. 10, which depicts the input of carbon dioxide, the output of methane and the pH of a reaction system in accordance with the present invention over a period of 42 hours. Where carbon monoxide is present, the flow of hydrogen may be adjusted in order to maintain a ratio of a combination of carbon monoxide and carbon dioxide to hydrogen of between about 18:82 and about 30:70. Alternatively, the flow of hydrogen is adjusted in order to maintain a ratio of carbon monoxide to hydrogen of about 25:75.

The pH of the liquid medium may be monitored, for example continuously monitored; this may be achieved by means of a probe within the reaction vessel. The amount of carbon dioxide flowing into the reaction vessel may be adjusted in accordance with the measurement of pH. The adjustment to the amount of carbon dioxide entering the reaction vessel may be an adjustment made to the rate of flow of a separate source of carbon dioxide, or to the rate of flow of a gaseous composition, or both.

Carbon dioxide is also used by the microbial population to grow and divide. Consequently, the flow of carbon dioxide into the reaction vessel may be adjusted in order to alter the rate of growth of the microbial population. The adjustment to the amount of carbon dioxide entering the reaction vessel may be an adjustment made to the rate of flow of a separate source of carbon dioxide, or to the rate of flow of a gaseous composition, or both.

In some embodiments, the flow of carbon dioxide into the reaction vessel is determined on the basis of determinations of at least two of: the pH of the reaction medium; the level of carbon dioxide within a gaseous composition; and the density of the microbial population within the reaction vessel. In some embodiments, the flow of carbon dioxide into the reaction vessel is determined on the basis of determinations of all three criteria.

The carbon dioxide used in the present invention can be from any suitable source, for example as a by-product of various industries. Industrial carbon dioxide sources include but are not limited to: cement production, iron/steel production, chemical/petrochemical industry, pulp and paper industry, combustion of hydrocarbons.

The hydrogen used in the present invention can be from any suitable source. In embodiments in which methane is being produced as a means of storing energy, the hydrogen can be produced by a water electrolysis unit powered by a renewable electricity source and/or the electricity grid. For example, when using a renewable energy source, the water hydrolysis unit may be powered by the off peak or excess electricity produced by the renewable energy source. A by-product of the water electrolysis unit is oxygen.

Figure 8:
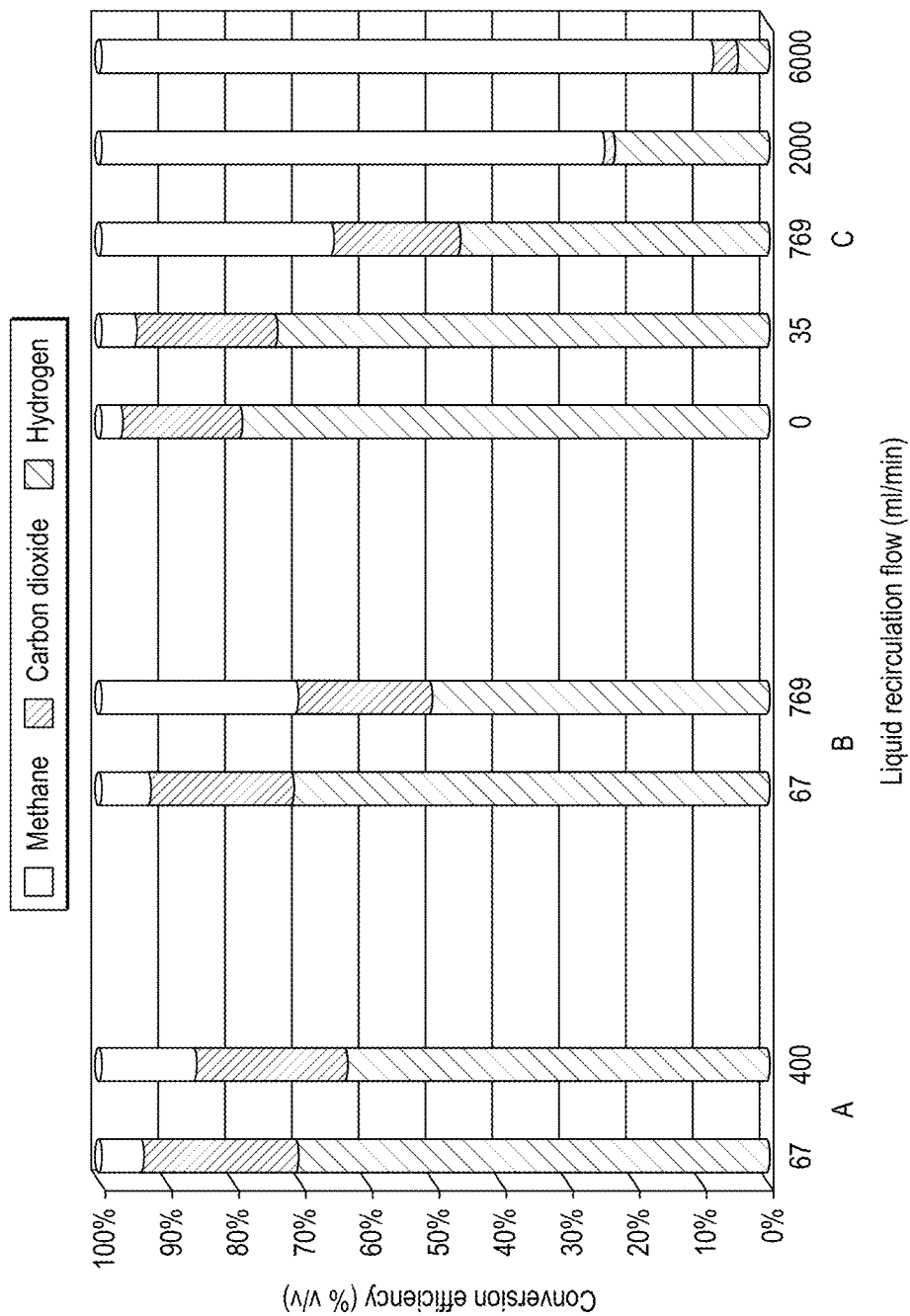
FIG. 8 shows a graph of the carbon dioxide to methane conversion efficiency of a system in relation to the liquid recirculation flow within the reaction vessel.

Preferably, the liquid medium is continuously circulated within the reaction vessel, for example by means of a pump. In some embodiments, the pump will be a centrifugal pump, which may continuously re-circulate the whole volume of the liquid medium, for example by extracting it from a lower point and re-introducing at a higher point into the reaction vessel through a pipe positioned on the outside of the reaction vessel. Circulation of the liquid medium enables a greater conversion of the carbon dioxide to methane. This is shown in FIG. 8, which depicts a graph of the carbon dioxide to methane conversion efficiency of a system in relation to the liquid recirculation flow within the reaction vessel. Sections A, B and C of the graph indicate 3 different dates.

The optimum rate of recirculation will depend upon a number of factors, comprising the microbial concentration within the medium, whether the microbial population is attached to a solid substrate, and the methane quality required. Recirculation of liquid media turnover rates between 4000 and 9000 litres per litre of microbial culture per day have provided good conversion efficiencies; however, flowrates can be further increased or decreased if beneficial.

The gases may be introduced into the reaction vessel by any means known in the art, and may be introduced into the liquid medium by means of mechanical and/or electrical driving force (for example via use of a pump, injector, diffuser or blower). In addition to circulating the liquid, the pump, e.g. the centrifugal pump, may suck in the gases entering the reaction vessel as it enters the reaction vessel, or shortly thereafter, and mix it with the liquid medium. The drag force that is created in the main body of the reaction vessel as a result of the motion of the liquid counteracts the buoyancy force applied on the bubbles created by the gases mixing by the liquid medium, thus retaining the gases for longer periods in the liquid medium. Disengagement of the product gas from the liquid is also an advantage brought by this centrifugal pump and allows a good dispersion of the microbial culture through the reactor vessel.

In some embodiments, the gases may enter the reaction vessel via one or more diffusers, for example microporous diffusers. However, diffusers that are typically used in aeration systems have an intrinsic limitation. The bubbles formed at the pores obey Tate's Law: $W=2\pi r \gamma$; where: W is the mass of the bubble; r is the radius of the pore and $\gamma$ is the surface tension. The high surface tension of water guarantees that the diameter of the bubble leaving the diffuser will always be larger than the diameter of the pore. Also the pores tend to block over time either from impurities in the gas stream or from deposition of insoluble salts or microbial attachment which decreases the diffuser's efficiency.

Preferably, the bubbles formed by the gas entering the liquid medium are bubbles with an average diameter of about less than about 1 mm. In some embodiments, the bubbles have an average size of less than about 800 µm. In some embodiments, the bubbles have an average diameter of less than about 600 µm. In some embodiments, the bubbles have an average diameter of less than about 400 µm. In some embodiments, the bubbles have an average diameter of less than about 200 µm. Constant re-circulation of the gas-liquid mixture may result in the formation bubbles, although bubble formation may be improved dependent upon the pump circulating the liquid medium. For example, centrifugal pumps have been proven efficient in their ability to form bubbles with an average diameter of less than 1 mm, mainly due to the fact that they use impellers of small diameters and high angular velocities. In the present invention, the impeller may not only accelerate liquid flow but may also serves as a gas-liquid blender. Cavitation phenomena might also be present, depending mainly on the rotational speed, the shape of the impeller, the flow-rate of the feeding gas and the hydrostatic pressure difference between the entry and exit points of the recirculated liquid. Cavitation enhances gas diffusion but at the same time might have a destructive effect on the microbial cells that pass through the pump; consequently a means of microbial attachment, for example attaching the microbes to a solid substrate, might be required depending on the type of pump and rotational speeds used.

The formation of bubbles with an average diameter of less than 1 mm improves gas-liquid mass transfer as bubble size is inversely proportional to the total surface area of contact between the gas and liquid phase, and also because the buoyant forces applied on a bubble are proportional to the bubble's volume.

The conversion inside the biocatalysed methanation reaction vessel may occur at atmospheric pressure. The temperature at which the biomethanation is carried out is dependent upon the microbial population used; typically a mesophilic temperature of between about 35° C. and 38° C. may be used, but where the microbial population is thermophilic a temperature of between about 55° C. and 60° C. may be used. However, lower temperatures could also be possible.

For every mole of methane produced, 2 moles (36 ml) of water are also produced. This results in dilution of the liquid medium. Consequently, excess water should be removed from the reaction vessel. This may be done in a variety of known ways, although in many cases, removal of excess water will also lead to removal of nutrients, and in some cases microbes, so that additional nutrients, and in some embodiments, additional microbes, must be added to the reaction vessel. It is preferable though that excess water is removed from the reaction vessel via a means which does not remove nutrients or microbes.

Figure 3:
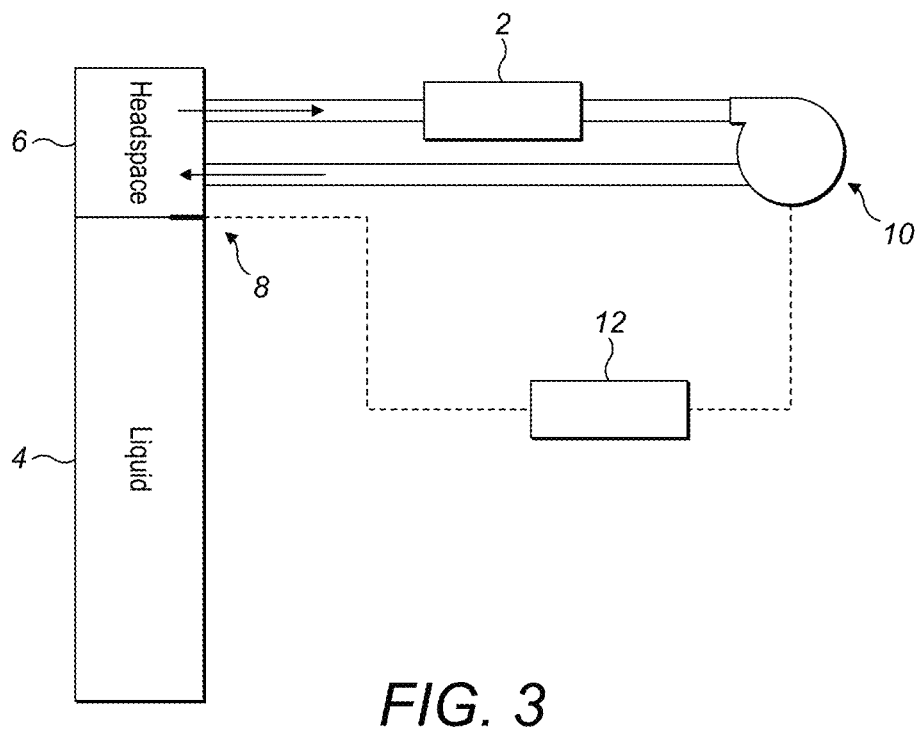
FIG. 3 shows a system for removing excess water from a reaction vessel without removing nutrients and microbes.

In some embodiments, the excess water is removed via means of a condensation or desiccation unit 2. This may be connected to the reaction vessel 4 at a point above the desired maximum level 6 of the liquid medium (FIG. 3). When the volume of the liquid medium increases to a predetermined level a sensor 8 sends a signal that activates a fan, a suction device or a blower 10 (in FIG. 3 this is shown as signal from sensor 8 activating power switch 12, which activates device 10). The device 10 extracts the gas from the headspace within the reaction vessel 4 and carries it through the condenser/desiccator 2 before reintroducing it into the reaction vessel 4, thus keeping the mass of water in the liquor constant. Removal of liquid in this manner means that there is no loss of nutrients or microbes from the medium, and so additional nutrients and microbes need not be added to the liquid medium in such systems.

Figure 4:
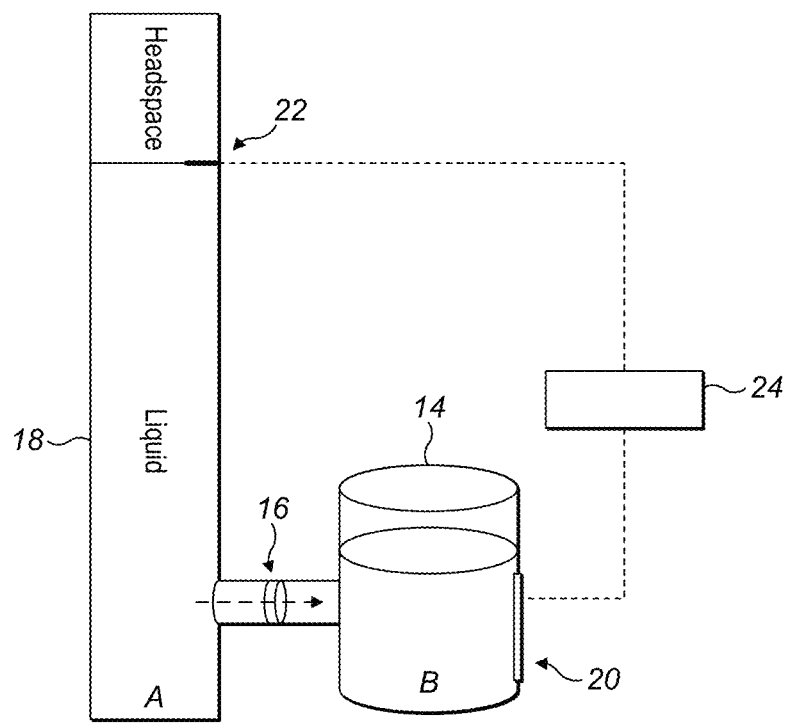
FIG. 4 shows another system for removing excess water from a reaction vessel without removing nutrients and microbes.

In some embodiments, for example as shown in FIG. 4 a container 14 with liquid with a solute concentration (e.g. water with a salt concentration) of greater osmotic potential than that of the liquid medium in the reaction vessel (solution B) is attached to a port at the side of the reaction vessel. The solute may be a salt, and the salt may be any salt which is soluble in water; for reasons of convenience, sodium chloride may be used. Typically the solute concentration will be significantly greater than that of the liquid medium, for example 2, 4, 10 or 20 times higher. An osmosis membrane 16 separates the concentrate in the container 14 from the liquid in the reaction vessel 18. The membrane 16 has a pore size of a few Å (for example, less than about 5 Å) which makes it permeable to water and gas molecules whilst remaining impermeable or substantially impermeable to metal ions and any macromolecules. The rate of movement of water from A to B is controlled by the concentration of the solution B, and so the solute concentration may be adjusted in order to control the extent of the removal of water from the reaction vessel. In addition to or as an alternative to adjusting the solute concentration, the pressure in either or both of the reaction vessel 18 or the container 14 may be adjusted, in order to control the rate of the removal of water from the reaction vessel 18; for example, the pressure in container 14 may be reduced in order that more water is removed from the reaction vessel 18. In some embodiments, the solute concentration of solution B may be controlled, for example, by evaporation induced via means of a heating element 20. In some embodiments, as shown in FIG. 4, the activation and deactivation of the heating element 20 may be controlled by a sensor 22 which determines the surface level of the liquid inside the reaction vessel. In FIG. 4 this is shown via the sensor 22 controlling power switch 24 which activates heating element 20. Removal of liquid in this manner also ensures that there is no loss of nutrients or microbes from the medium, and so additional nutrients and microbes need not be added to the liquid medium in such systems.

Figure 5:
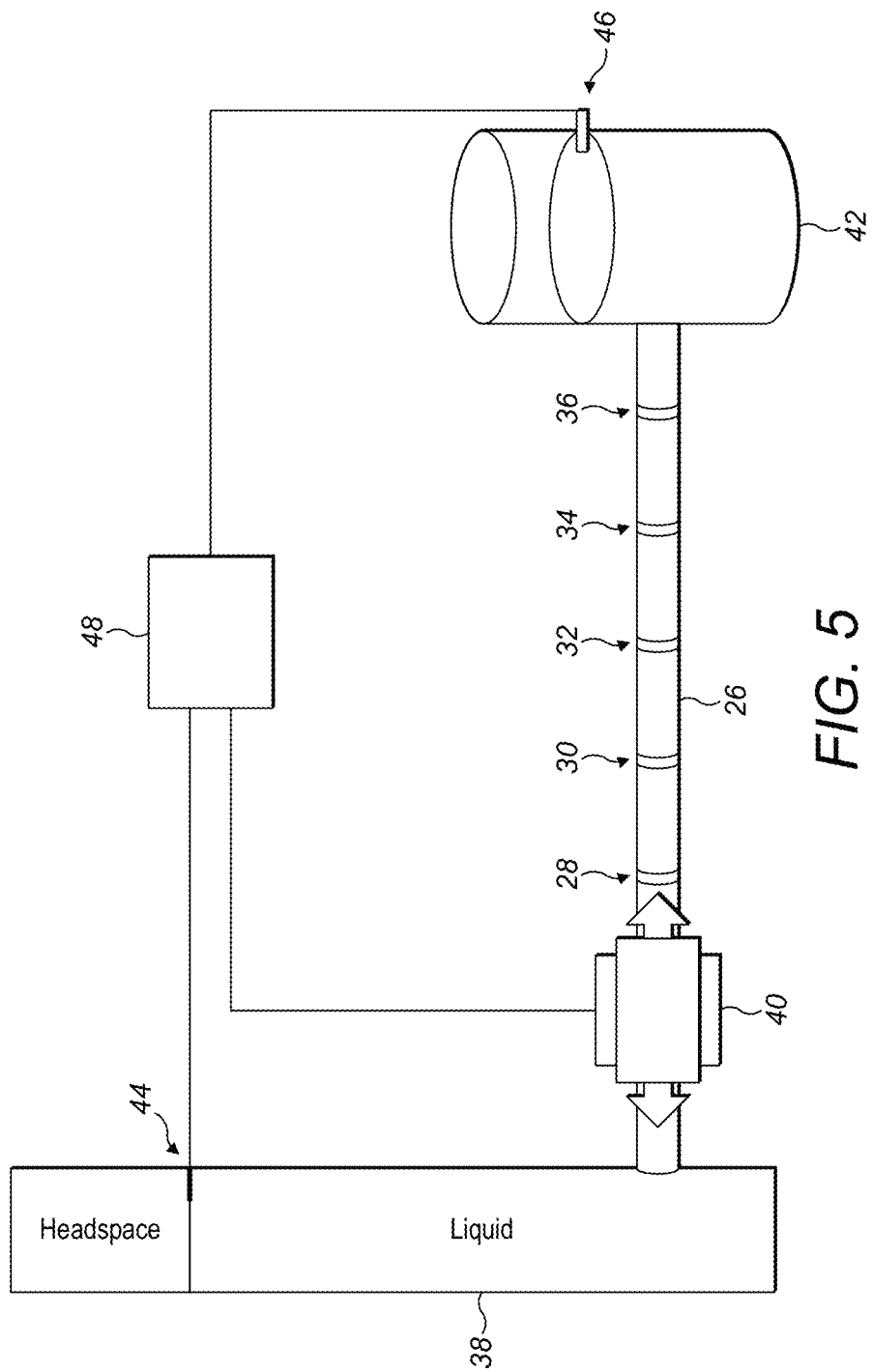
FIG. 5 shows another system for removing excess water from a reaction vessel without removing nutrients and microbes.

A further system for the removal of excess water is shown in FIG. 5. A filtration device 26 can comprise of a series of filters of decreasing pore size (for example decreasing from particle filtration 28 to micro-filtration 30 to ultra-filtration 32 to nano-filtration 34 to osmosis 36) attached to a port on the reaction vessel 38. A pump 40 may drive the liquid through the lumen of the filtration device 26 towards a tank 42 for pure water collection. The pump is a reversible pump, and backwash cleaning of the filters can be accomplished by the reverse flow function of the pump. The activation, and direction of the pump may be controlled by sensors 44 and 46 which detect the level of liquid in the reaction vessel 38 and the tank 42, and which activate a control switch 48 accordingly. Such a system also ensures that there is no loss of nutrients or microbes from the medium, and so additional nutrients and microbes need not be added to the liquid medium in such systems.

As the microbial conversion takes place and because of the continuous gas feeding, the positive pressure created pushes the gas produced through a port at the top of the reaction vessel and through a series of sensors for gas analysis and gas flow measurement. The output gas may then be analysed to determine if the methane content is sufficiently high. If not, it may be passed back through the system to further increase the content of methane, or it may be used to reduce the overall energy costs of the system, for example via means of a combined heating and power ("CHP") system. If the methane content is sufficiently high, the output gas may be used as intended, e.g. stored for future use as a power source.

The present invention provides means for biomethantion in which the efficiency of conversion of carbon dioxide to methane is at least 95%. In some embodiments, the efficiency of conversion of carbon dioxide to methane is at least 99.7%. An output of methane of at least 1.9 litres, or at least 3.2 litres of methane per gram of volatile solids per day may be achieved. A conversion of 120 litres of hydrogen and carbon dioxide per litre of microbial culture per day into 24.2 litres of methane per litre of microbial culture per day can take place; and when two subunits are placed in series a conversion of 200 litres of hydrogen and carbon dioxide per litre of microbial culture per day into 40.65 litres of methane per litre of microbial culture per day can be achieved.

This provides a significantly improved efficiency over known systems which utilise cultures of enriched hydrogenotrophic methanogens.

FIG. 1 depicts an example of a system in which the concentration of methane within a biogas may be increased. A biogas sourced from any of an anaerobic digestion ("A.D.") plant, gasification plant, pyrolysis plant, coal bed gas, coke oven gas and landfill gas is stripped of impurities before passing into a gas content analysis unit which analyses the content of the gas for levels of carbon dioxide, hydrogen and methane. The biogas then moves into a biomethanation unit (i.e. a reaction vessel). Data from the gas content analysis unit is sent to a gas flow controller unit, which determines the rate at which any additional carbon dioxide and hydrogen should be added. Carbon dioxide then moves from the carbon dioxide source at the determined rate into the biomethanation unit, and hydrogen from a water electrolysis unit passes into the biomethanation unit at the determined rate. The water electrolysis unit is shown as being powered by either a renewable energy source or the electricity grid. In the example of FIG. 1, the carbon dioxide and hydrogen are mixed prior to entering the biomethanation unit; whilst this may occur in some embodiments, this is not a necessity of the invention. Excess water is removed from the biomethanation unit by a water removal unit, which preferably does not remove nutrients or microbes from the biomethanation unit. The biogas with increased methane content is forced out of the biomethanation unit and passes to an analysis unit. Rejected gas is stored onsite, and may be passed to a CHP unit which helps power and heat the system. Approved gas is then ready for storage or use.

Figure 2:
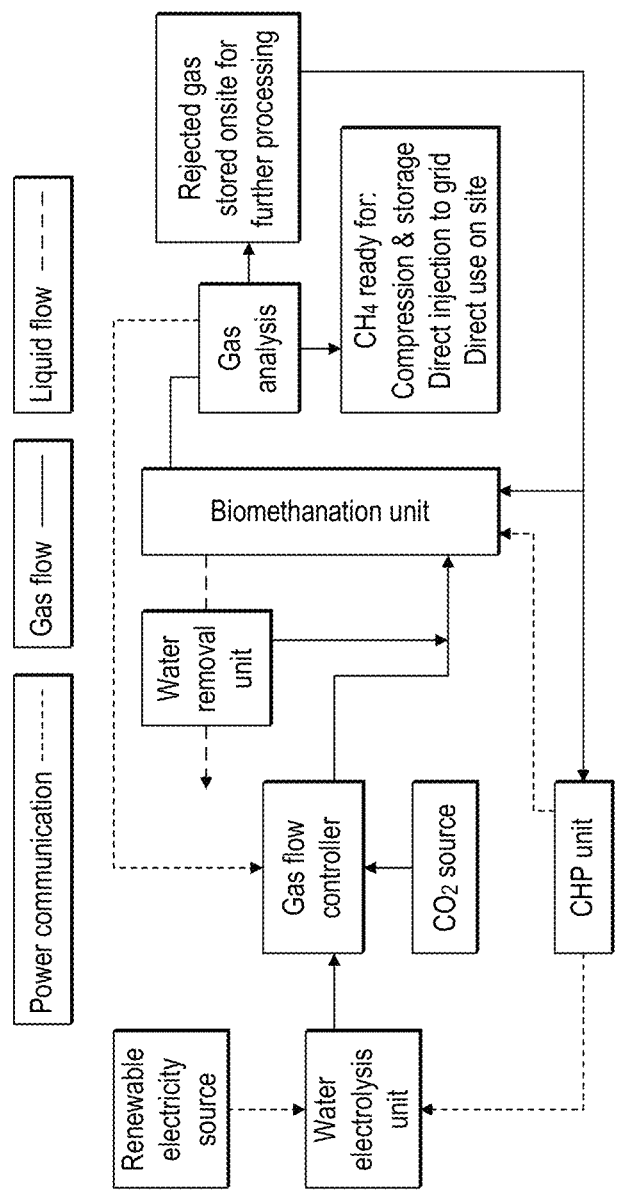
FIG. 2 shows a system in which biomethanation is used as a means of storing energy produced from renewable sources.

FIG. 2 depicts a system in which biomethanation is used as a means of storing energy produced from renewable sources. Electricity produced by the renewable energy source is used to power a water electrolysis unit. The hydrogen produced by the water electrolysis unit then passes to a gas flow controller, as does carbon dioxide from a carbon dioxide source. The gas flow controller unit determines the concentrations of each gas which should be sent to the biomethanation unit, and the hydrogen and carbon dioxide are then sent to the biomethanation unit. Excess water is removed from the biomethanation unit by a water removal unit, which preferably does not remove nutrients or microbes from the biomethanation unit. The biogas with increased methane content is forced out of the biomethanation unit and passes to an analysis unit. Rejected gas is stored onsite, and may be passed to a CHP unit, which helps power and heat the system. Approved gas is then ready for storage or use.

Figure 6:
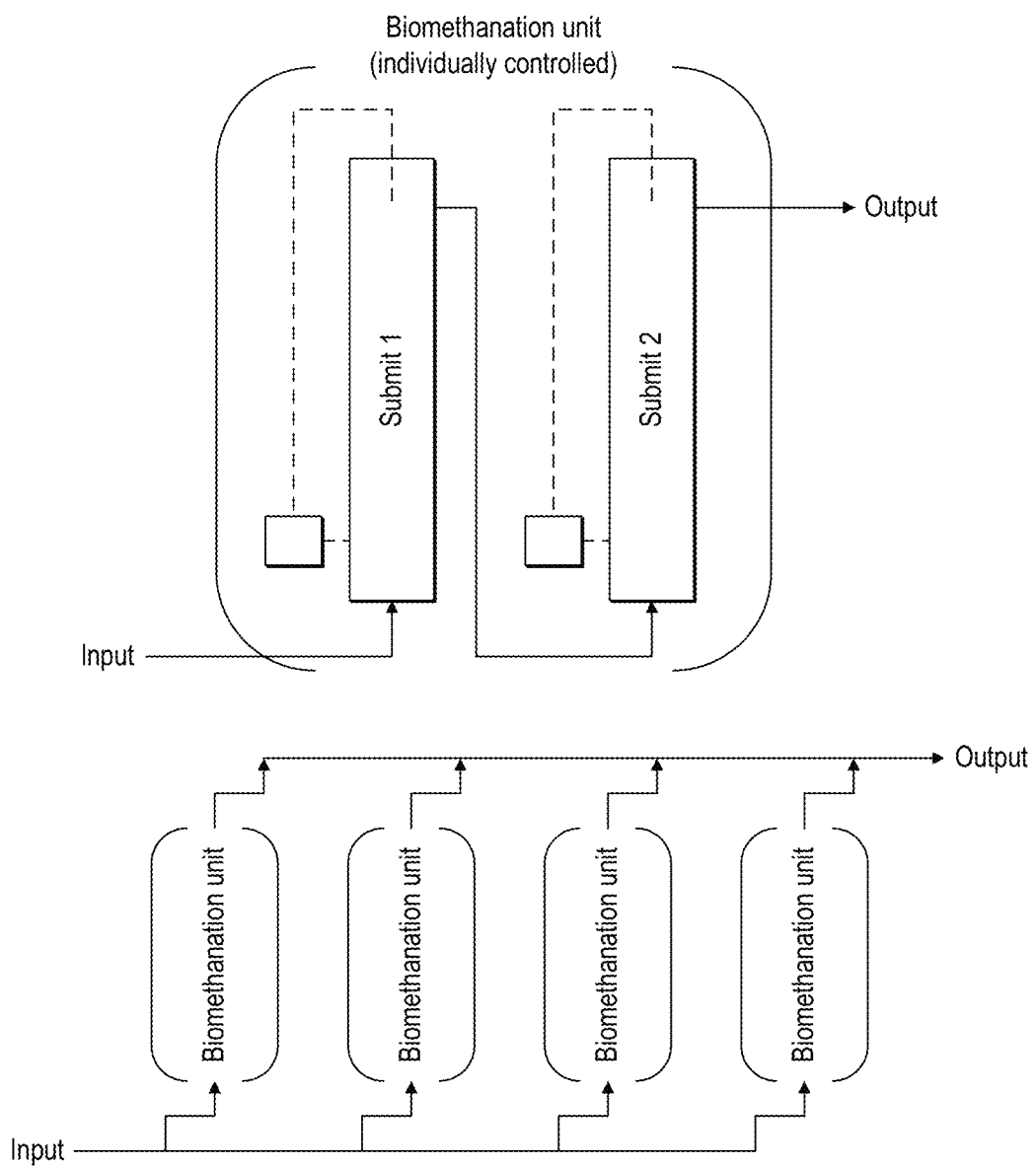
FIG. 6 shows the upscaling of systems of the present invention.

The systems and methods of the present invention may be upscaled by connecting a plurality of biomethanation units in sequence (connected in series and/or in parallel) as shown in FIG. 6.

Figure 7:
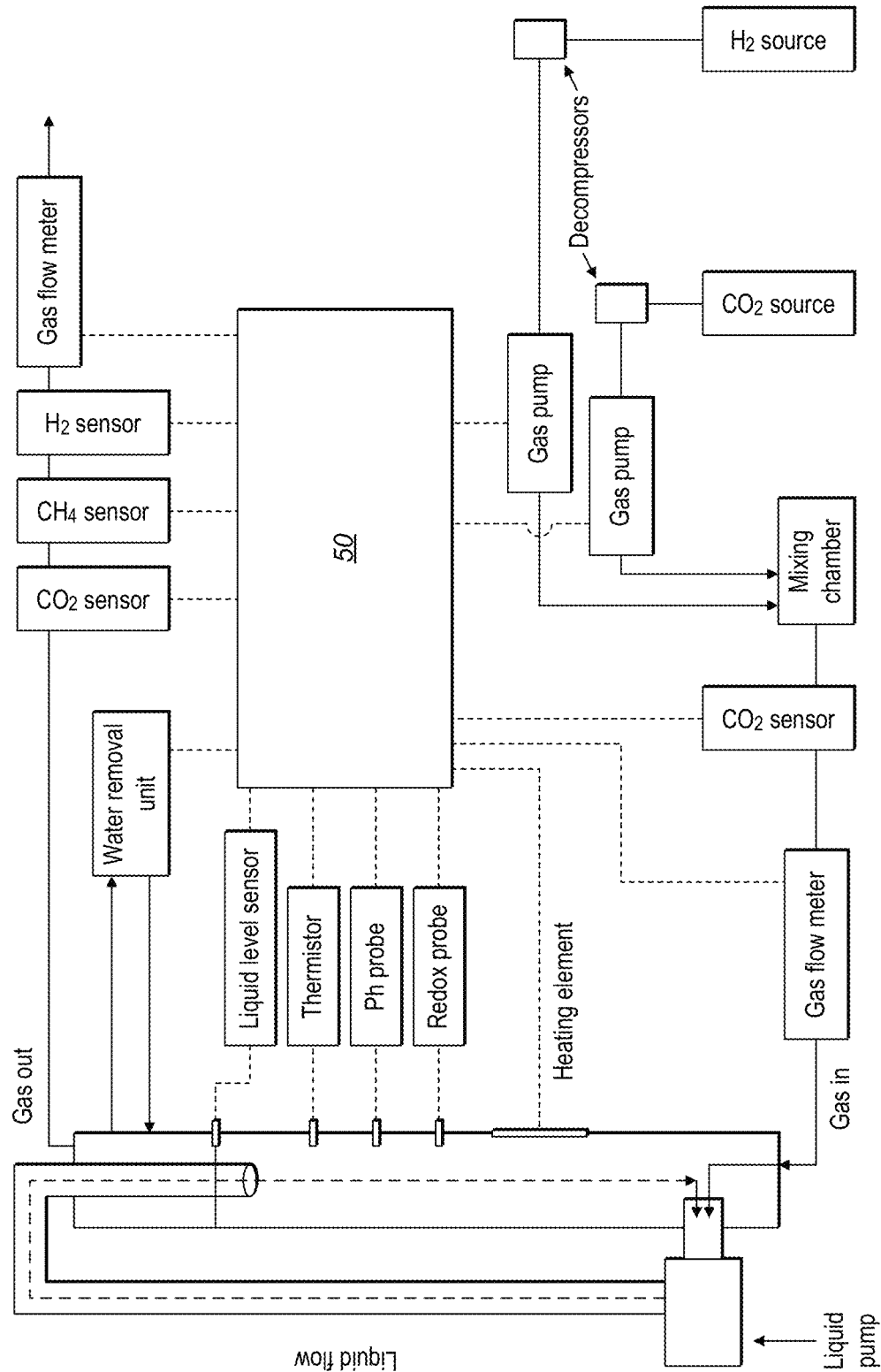
FIG. 7 shows a system in which a single control unit 50 is used to monitor and communicate various parameters and control gas flows and water removal.

FIG. 7 depicts a system in which a single control unit 50 is used to monitor and communicate readings of liquid levels, temperature, pH, redox, gas composition, determine gas flow and control water removal. Hydrogen and carbon dioxide are pumped into a mixing chamber under the control of control unit 50 so as to provide a mixture with the desired ratio of hydrogen to carbon dioxide. Prior to this, the gas lines pass through a decompression system in order for the gases to reach atmospheric pressure. The mixture then passes through a carbon dioxide sensor, which passes data back to control unit 50 so as to confirm that the expected quantity of carbon dioxide is being passed to the reaction vessel via a gas pump under the control of control unit 50. As a result the specified carbon dioxide to hydrogen ratio and feeding flow are continually achieved.

The mixture then flows into the reaction vessel, under the control of the control unit 50. The liquid in the reaction vessel is circulated via a liquid pump. The temperature, pH and redox of the liquid medium, and the level of the liquid within the reaction vessel, are detected by probes or other sensors attached to the reaction vessel, with the data being passed to control unit 50. Excess water is removed by an excess water removal unit under the control of control unit 50. Gas passes out of the reaction vessel and moves through carbon dioxide, methane and hydrogen sensors, with the data being passed on to control unit 50. The gas is then sent to the requisite destination under the control of control unit 50.

Using a system substantially as shown in FIG. 7, the specific hydrogenotrophic methanogenic activities were measured for the microbial cultures before and after an enrichment process as described herein. The pre-enrichment microbial population produced on average 0.06 litres of per gram of volatile solids per day. The post-enrichment microbial population in contrast produced 3.2 litres of methane per gram of volatile solids per day. The enriched culture in the system of FIG. 7 was then able to operate at an efficiency in which there was the output gas consisted of approximately 99.7% methane; with an influent gas (hydrogen and carbon dioxide) throughput of 200 litres per litre of microbial population within the reactor vessel per day; and an outflow gas throughput of 40.65 litres of methane per litre of microbial population within the reactor vessel per day. This provides a reasonable conversion rate with a yield of very high methane output quality, which requires an industrial process with only a small footprint. However, further enrichment of the microbial culture would be possible. The microbial culture when fully enriched is expected to allow over 1200 litres of input gases per litre of reactor per day. Conversion may take place only in 1 reactor or in multiple and over 99.7% $CH_4$ output quality can be achieved.

Figure 13:
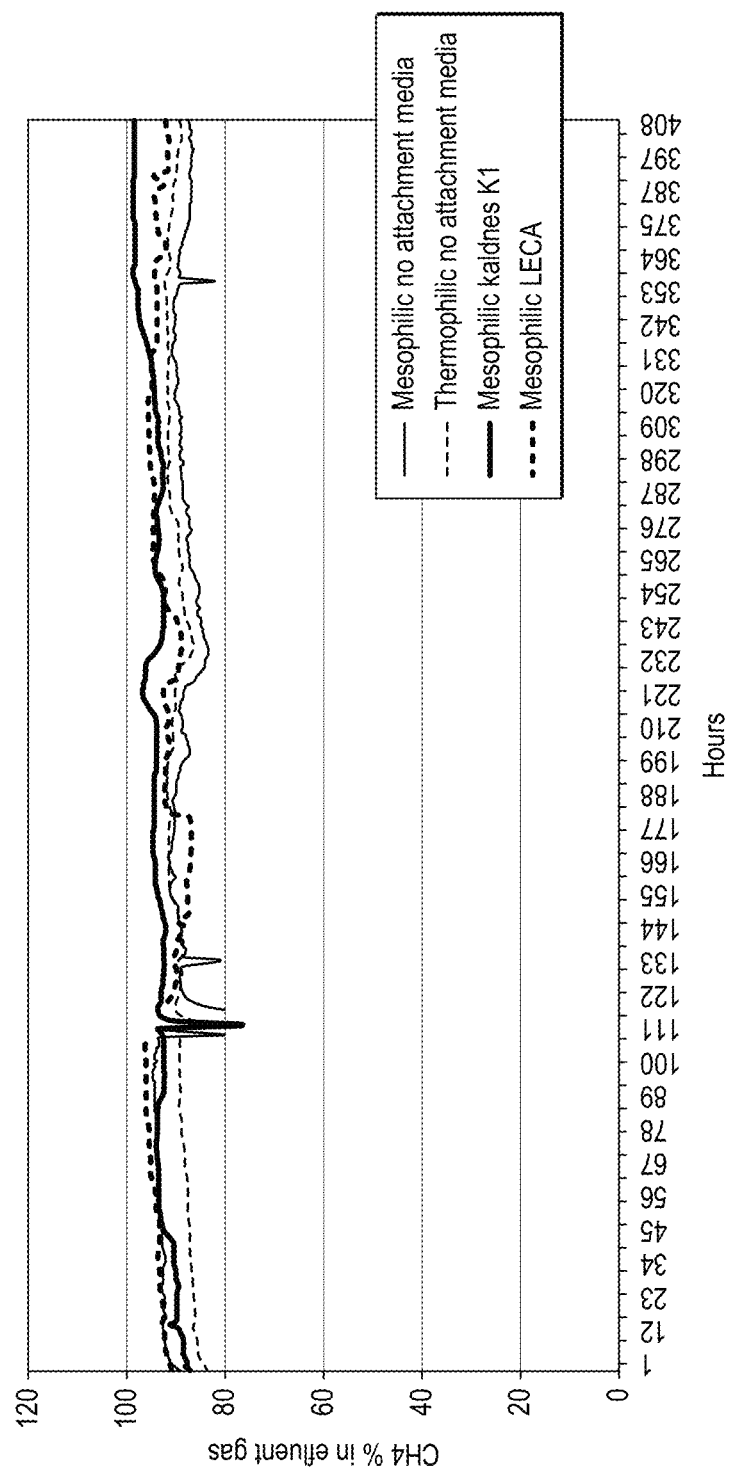
FIG. 13 shows the conversion efficiency of four different reactors under different conditions.
Figure 24:
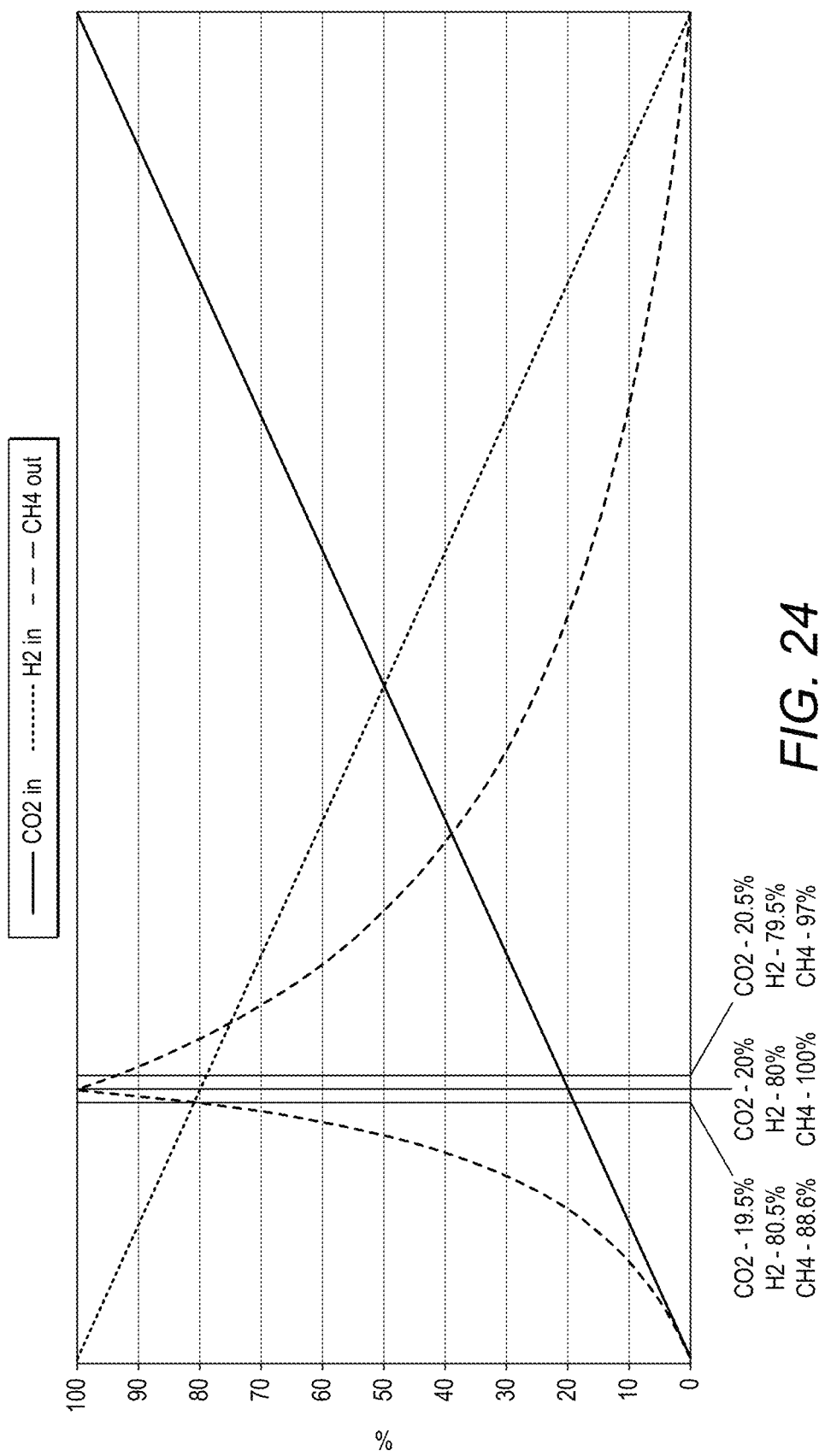

The present invention enables reasonably constant rates of conversion to methane to be preserved. Greater control and higher quality output is possible when using high quality mass controllers for gases input. FIG. 24 demonstrates the importance of precise input gas flows in conversion efficiencies. The importance of controlled input flow is greater in small reactors. FIG. 13 demonstrates the conversion efficiency of the invention. Four identical reactors were operated in parallel; one was kept at thermophilic conditions (55° C.) and three at mesophilic (37° C.). Biofilm attachment media were used in two of the mesophilic reactors, Kaldnes K1 (polyethylene wheels) in one and LECA (Light Expanded Clay Aggregate balls) in the other. No attachment media were used in the third mesophilic reactor as well as in the thermophilic reactor. The same liquid recirculation system was used for each reactor. The graph displays conversion efficiency for a period of 400 hours of continuous operation at constant gas throughput of 36 v/v.d. By the use of real time gas control, the volumetric percentage of $CH_4$ in the effluent gas can be preserved at reasonably constant levels.

Figure 14:
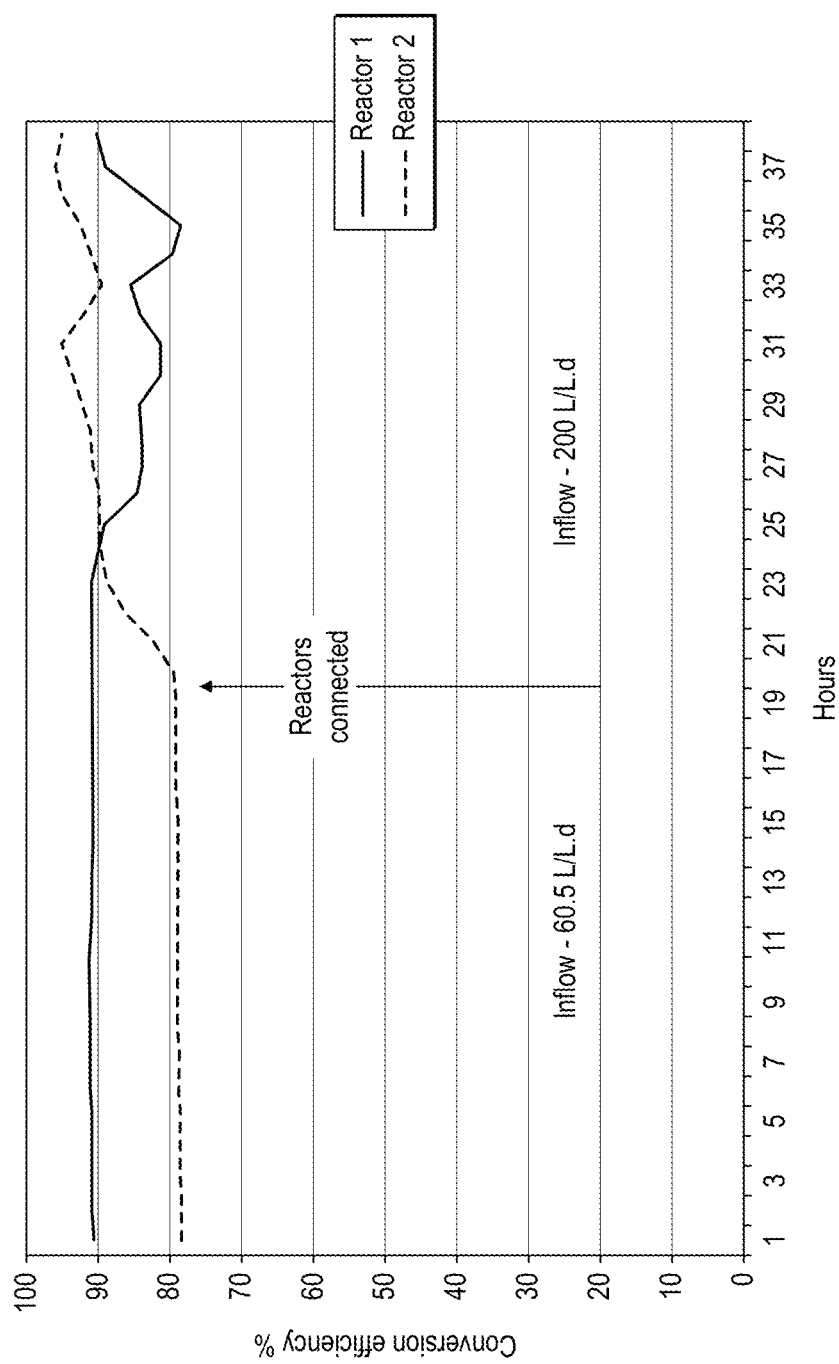
FIG. 14 shows the conversion efficiency of two reactor units before and after being connected in series, at different feeding gas flowrates, and in particular the biogas upgrading capabilities.

Two or more units can be connected in series when there is a higher rate of gas flow which needs to be converted. FIG. 14 shows the conversion efficiency of two units at different gas flow rates before and after connection. Before connection the total gas influent was 60.5 L/L.d. After connection the gas inflow was raised to 200 L/L.d whilst conversion efficiency was preserved. The microbial culture was still being enriched in both reactors.

Table 1 below shows the ability of the culture to work at different gas feeding flowrates and compositions whilst achieving constant conversion efficiencies. The microbial culture was still being enriched at this stage.

TABLE 1

Conversion efficiency at 3 different gas feeding rates for one of the mesophilic reactors ($CO_2/H_2 \sim 0.28$)

| Inflow $H_2/CO_2$ (L/L · d) | 51.8 | 60.5 | 200 |
|---|---|---|---|
| $CH_4$ % in outflow | 99.3 | 98.9 | 90.1 |

Figure 15:
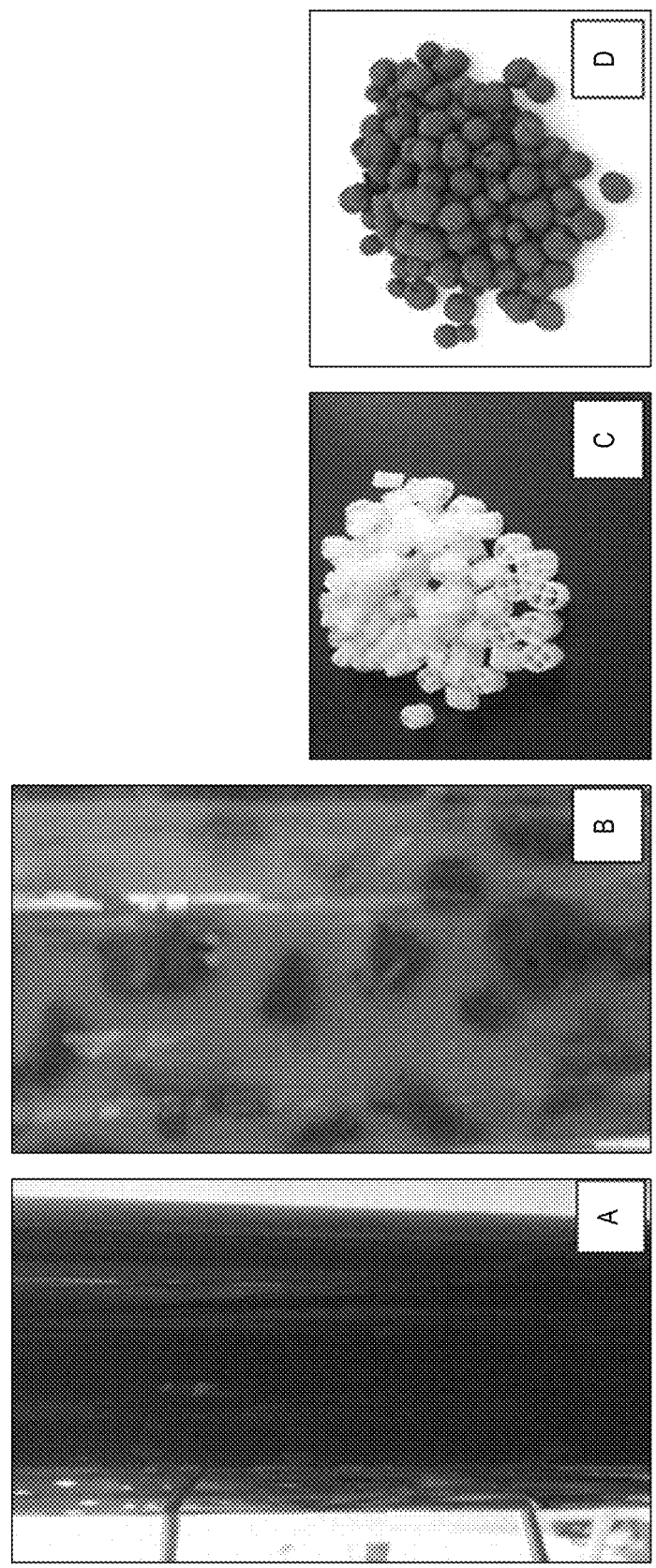
FIG. 15 shows the contrast between mesophilic reactors with and without attachment media, and the microbe attachment media before use.

Embodiments of the present invention enable the formation of biofilm within the reactor. Visible biofilm was formed in both the reactors containing the two different types of microbial attachment media (Kaldnes K1 and LECA) referred to in relation to FIG. 13. FIG. 15 displays the contrast between the mesophilic reactor containing the Kaldnes K1 material and the mesophilic reactor without any attachment media 4 weeks after inoculation. The high velocity of the fluid due to recirculation (6 L/min) did not have an adverse effect on biofilm formation. The biofilm started being visible in both carrier materials after a period of two weeks. During maturation, biofilm thickness remained unchanged which indicated that there was continuous detachment and renewal of colonisation.

As shown in FIG. 15, in (A), the reactors without attachment media, the colour of the liquid media is dark black, as all microbes are in suspension and continuously mixed. In (B), the reactor containing the attachment media, the colour of the liquid media is light brown as the majority of the microbes have been attached on the polyethylene pieces. (C) and (D) show the Kaldnes K1 and the LECA attachment media, respectively, prior to use.

Biofilm formation can have a significant impact on the dewatering of the liquid media. From (B) in FIG. 15 it is evident that the recirculated liquid has a much lower concentration of solids and therefore the liquid matrix is much easier to dewater by filtration. Furthermore, the attached microbes are not affected since they will not be passing through the dewatering system.

Figure 16:
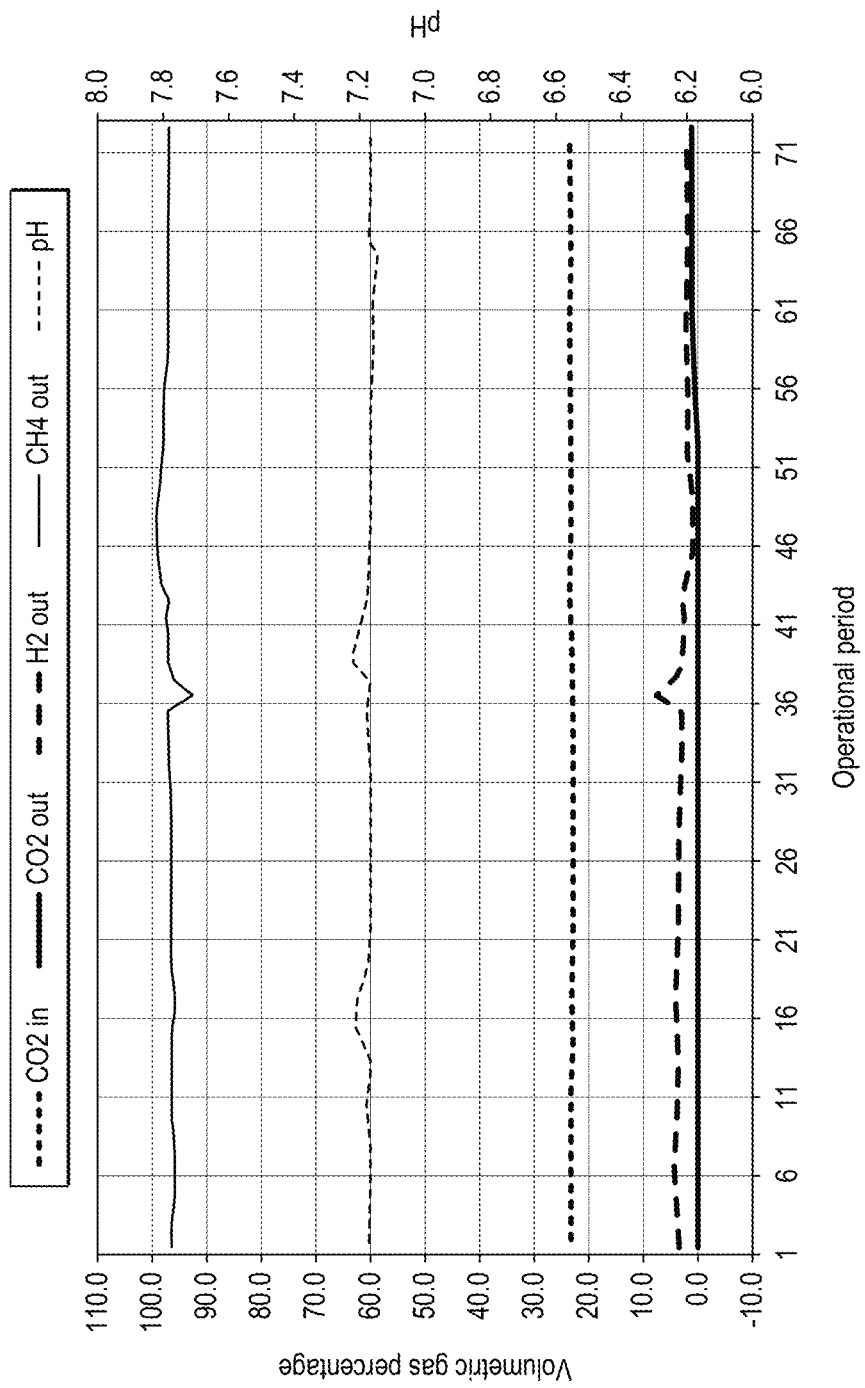
FIG. 16 demonstrates $CO_2$ dependent pH buffering.

The present invention also enables $CO_2$ dependent pH buffering. $CO_2$ depended pH buffering is possible when the volume of the injected $CO_2$ is close to the $CO_2$ to $CH_4$ conversion capacity of the system. FIG. 16 demonstrates that fine tuning buffering is possible by controlling the levels of $CO_2$ entering the system in relation to the data obtained at the time in terms of conversion efficiency and pH. This enables the buffering capacity of $H_2CO_3$ to be used to keep the pH at the desired constant without the need of further chemical pH regulation.

Figure 17:
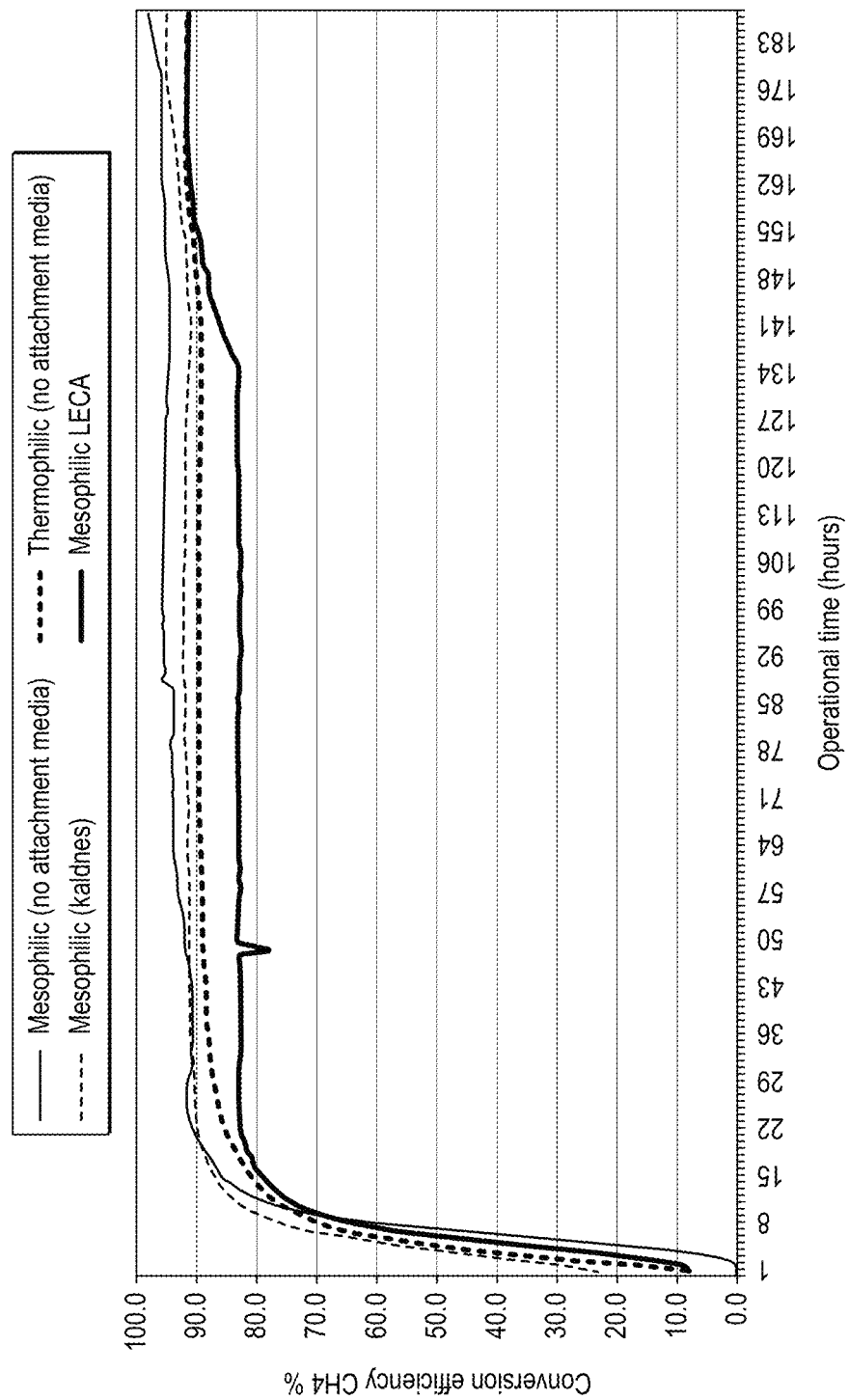
FIG. 17 shows the $CO_2$ to $CH_4$ conversion efficiency after a starvation period of 13 days.
Figure 18:
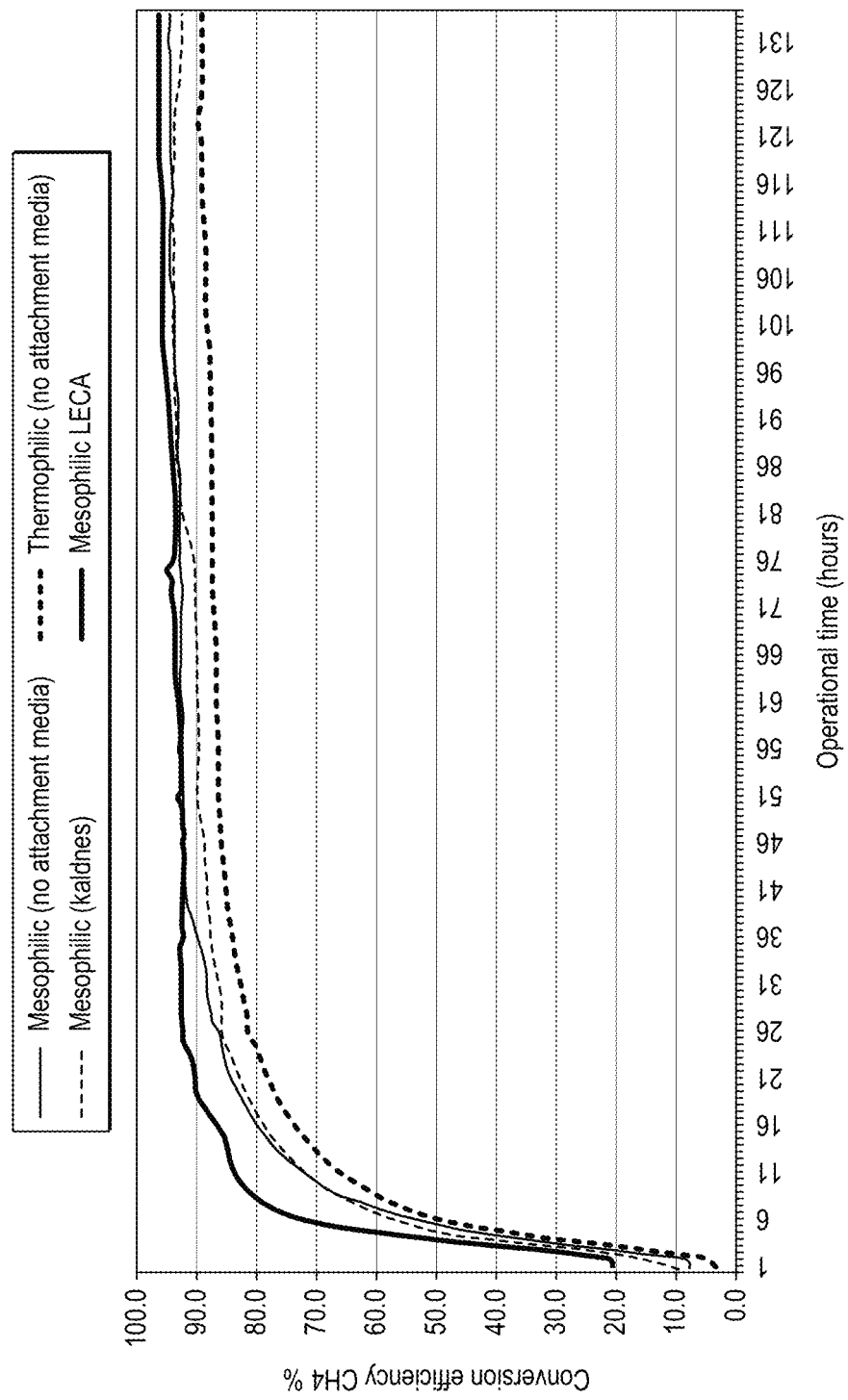
FIG. 18 shows the $CO_2$ to $CH_4$ conversion efficiency after a starvation period of 45 days.

Embodiments of the present invention are also capable of recovery from carbon/energy starvation. FIGS. 17 and 18 show the $CO_2$ to $CH_4$ conversion efficiencies of all four reactors referred to in relation to FIG. 13 after two starvation periods of 13 and 45 days, FIG. 17 depicting the recovery rate of all four reactors after 13 days of complete (carbon/energy) starvation, and FIG. 18 depicting the recovery rate of all four reactors after 45 days of complete (carbon/energy) starvation Under the same gas feeding rates, the recovery times for both experiments are similar with an average period of less than 24 hours for all reactors to reach 80% conversion efficiency. A lower gas throughput would have allowed a higher % $CH_4$ production during the recovery period.

Figure 19:
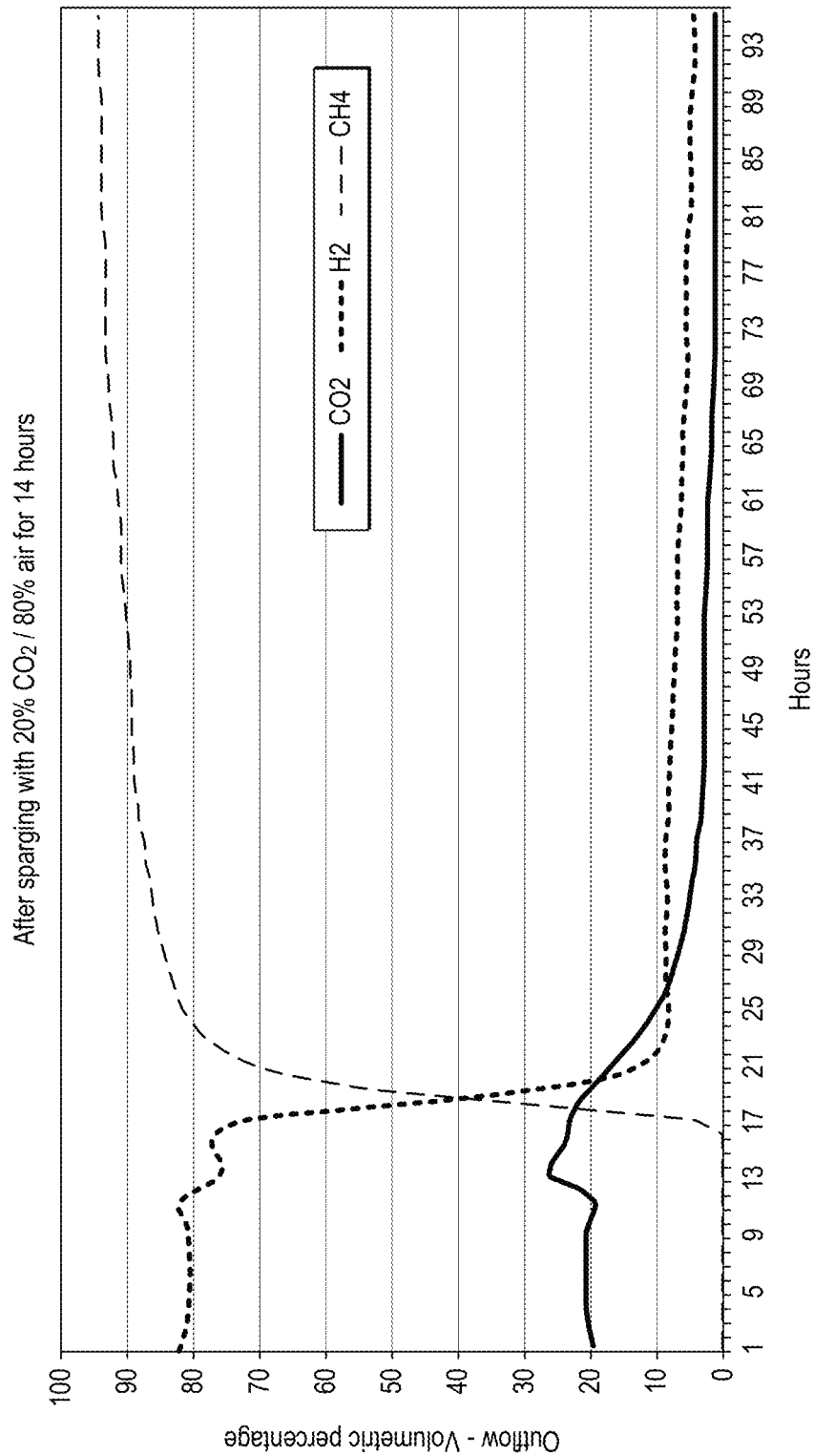
FIG. 19 shows the recovery of the conversion rate after the liquid media was exposed to oxygen.

Mixed cultures have an advantage over pure cultures, firstly due to the presence of facultative fermentative microbes that can scavenge dissolved oxygen and secondly due to the shielding mechanism of biofilms (in those embodiments in which biofilms are formed) as methanogens may have protection behind layers that act as diffusion barriers. To test the effect of oxygenation, the liquid media of one of the mesophilic reactors was sparged with a gaseous mix of 20% $CO_2$/80% air v/v for 14 hours before returning to a 78/22 $H_2/CO_2$ environment. FIG. 19 shows that recovery was complete after less than 24 hours.

Gas hold up is an important parameter in microbial gas conversion systems since it dictates the period of time that the culture will be in contact with the gaseous substrate. The speed of liquid recirculation directly affects gas hold up and consequently the rate of gas-liquid mass transfer. This is evident in FIGS. 20 and 21 which relate conversion efficiency to liquid recirculation flow.

Figure 20:
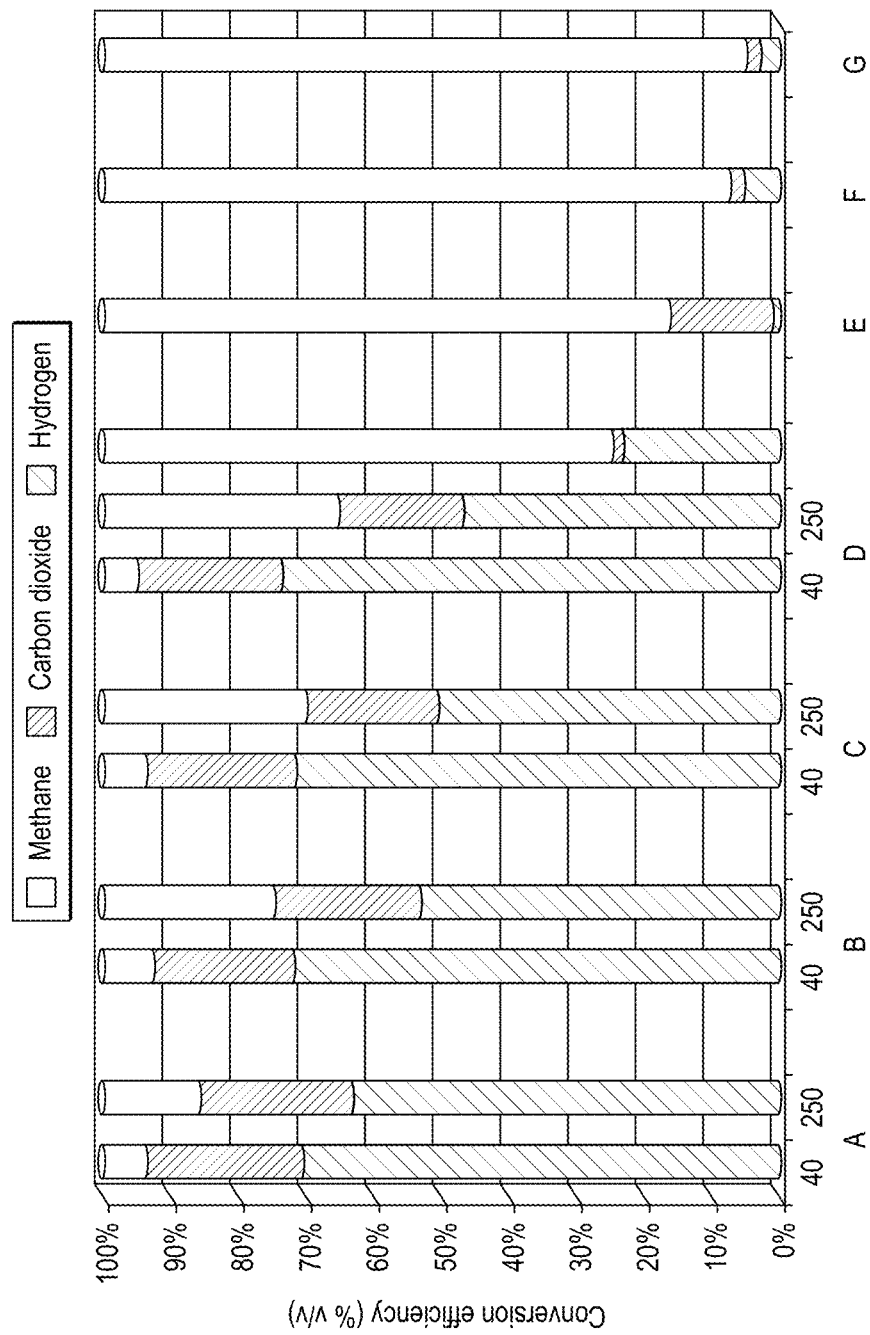
FIG. 20 shows the percentage of $H_2$, $CO_2$ and $CH_4$ in the effluent relative to liquor recirculation flow.
Figure 21:
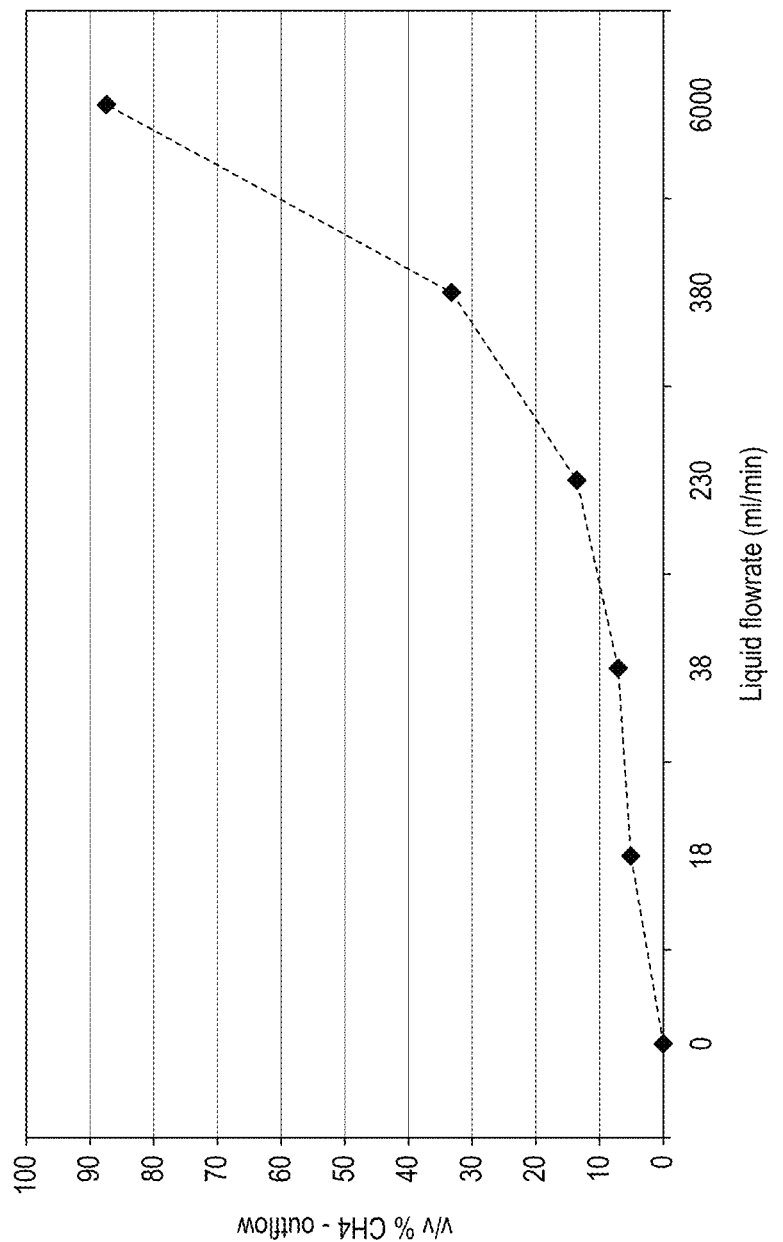
FIG. 21 shows the volumetric percentage of methane in the outflow relative to liquid recirculation flow rate.

FIG. 20 depicts the percentage of $H_2$, $CO_2$ and $CH_4$ in the effluent relative to the liquor recirculation flow. The data for A, B, C and D in FIG. 20 are derived from the use of a peristaltic pump operating at the speed (rpm) indicated below the column, with the exception of the third column in D for which the data were obtained after substitution with a centrifugal pump. The data for E, F and G were derived from the use of a centrifugal pump. This allowed smaller bubbles to form and also improved gas hold up. From this it can be seen that the speed of liquid flow recirculation is important in terms of conversion efficiencies and that increased efficiency is achieved with the use of a centrifugal pump.

It can be seen that the conversion efficiency changed immediately after the change in recirculation speed. This meant that the microbes were ready to accept higher amounts of substrate which was not available to them at lower recirculation speeds. The effect of liquid recirculation on gas conversion efficiency can be more clearly seen in FIG. 21 which relates the volumetric percentage of $CH_4$ in the outflow to the flowrate of liquid recirculation. The curve indicates that the gas diffusion is conversion rate limiting.

Figure 22:
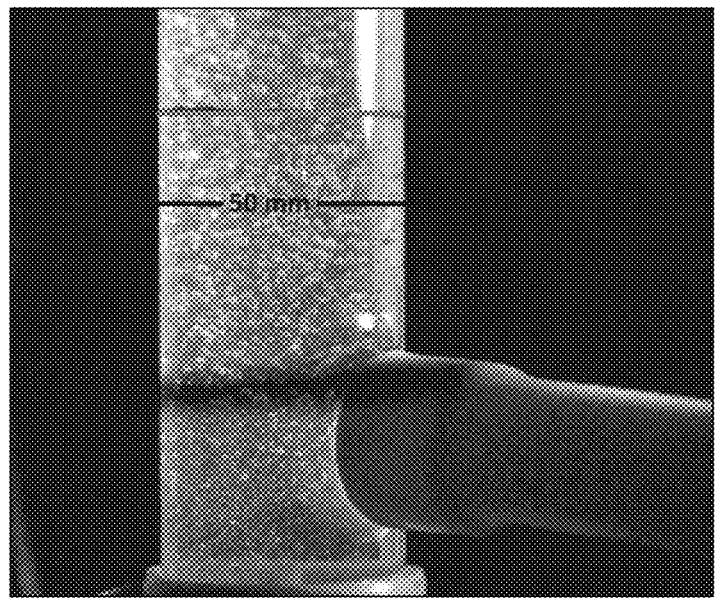
FIG. 22 shows the bottom part of the reactor when only water (liquid matrix) and air as the gaseous input were used for the demonstration
Figure 23:
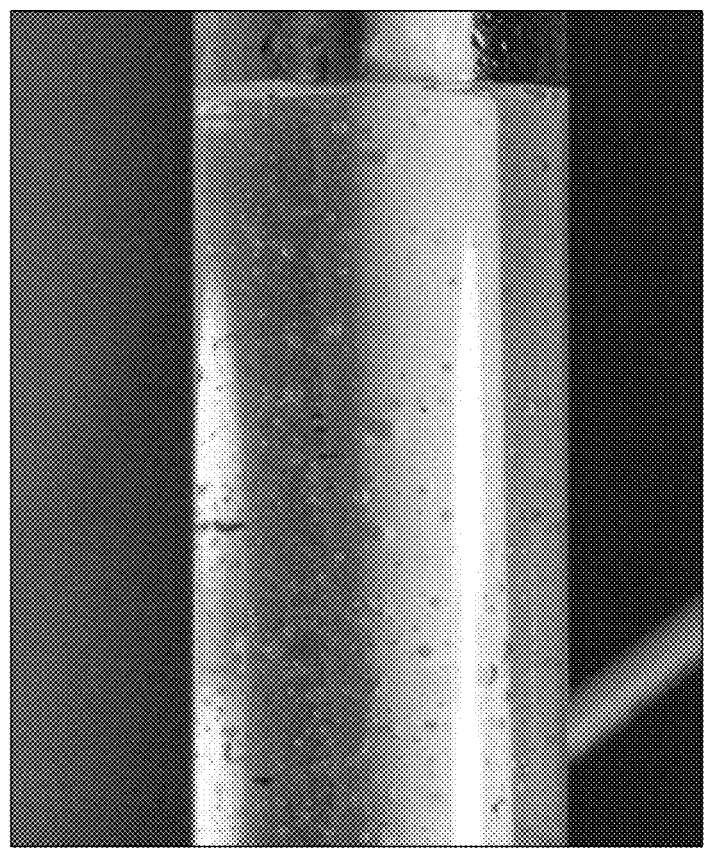
FIG. 23 shows the top part of the reactor when only water (liquid matrix) and air as the gaseous input were used for the demonstration FIG. 24 demonstrates the importance of precise input gas flows in conversion efficiencies.

FIGS. 22 and 23 are high resolution images of the bottom and top of the reactor with only water inside the reactors and with a recirculation occurring at 6 L/min while air was injected into the reactor at regular intervals. FIG. 22 depicts the bottom part of the reactor; the horizontal tubing connected to the glass column is the outlet from the reactor where the liquid enters the pump. Gas bubbles are forced to travel downwards and pass through the pump multiple times. FIG. 23 depicts the top part of the reactor. The bubbles in FIG. 23 travel upwards and represent the volume of the gas escaping to the liquid surface.

There is clear difference between the volume of the gas that gets drawn into the pump and the visible volume of gas escaping to the surface. The pictures were shot at the same time frame. The centrifugal pump induces turbulence which assists with gas-liquid mixing and facilitates the break-up of the bubbles. Other mixing devices can be facilitated to induce thorough gas-liquid mixing and turbulence (e.g. gas-liquid cyclone mixers, venturi mixers).

In addition, the present invention provides the following embodiments:

A. A system for biomethanation in which a microbial population produces methane using carbon dioxide and hydrogen as substrates, wherein the system comprises a reaction vessel, said reaction vessel comprising at least one inlet for enabling carbon dioxide, hydrogen and a gaseous composition comprising carbon dioxide and any of carbon monoxide, hydrogen, nitrogen, and one or more hydrocarbons, along with any trace components contained therein, to enter the reaction vessel; wherein the system comprises sensors for monitoring the amount of carbon dioxide within the gaseous composition prior to entering the reaction vessel, and wherein said system is capable of adjusting the flow rate of carbon dioxide in response to the level of carbon dioxide so detected so as to maintain at least one desired parameter within the reaction vessel. In some embodiments, the at least one desired parameter is the pH of the liquid medium within said reaction vessel. In some embodiments, said system is capable of adjusting the flow rate of hydrogen in accordance with the level of carbon dioxide detected in said gaseous composition; and in a further embodiment said system is capable of adjusting the flow rate of hydrogen in order to maintain a ratio of carbon dioxide to hydrogen of between about 18:82 and about 25:75. In some embodiments, the ratio is between about 22:78 and about 24:76. In some embodiments, either or both of the carbon dioxide and hydrogen concentrations may are less than 80, 60, 40, 20, or 10% of the total inlet gas stream.

B. A system for biomethanation in which a microbial population produces methane using carbon dioxide and hydrogen as substrates, wherein the system comprises a reaction vessel, said reaction vessel comprising at least one inlet for enabling carbon dioxide and hydrogen to enter the reaction vessel; wherein system comprises at least one sensor for monitoring the pH of the liquid medium, and wherein said system is capable of adjusting the flow rate of carbon dioxide accordingly so as to maintain a desired pH within the reaction vessel. In some embodiments adjusting the flow rate of carbon dioxide comprises adjusting the flow rate of a gaseous composition comprising carbon dioxide and any of carbon monoxide, hydrogen, nitrogen, and one or more hydrocarbons, along with any trace components contained therein. In some embodiments, said system is capable of adjusting the flow rate of hydrogen in accordance with the level of carbon dioxide detected in said gaseous composition; and in a further embodiment said system is capable of adjusting the flow rate of hydrogen in order to maintain a ratio of carbon dioxide to hydrogen of between about 18:82 and about 25:75. In some embodiments, the ratio is between about 22:78 and about 24:76. In some embodiments, either or both of the carbon dioxide and hydrogen concentrations may are less than 80, 60, 40, 20, or 10% of the total inlet gas stream.

C. A system for biomethanation in which a microbial population produces methane using carbon dioxide and hydrogen as substrates, wherein the system comprises a reaction vessel, said reaction vessel comprising a liquid medium, wherein said liquid medium is circulated continuously within the reaction vessel. In some embodiments, the liquid is circulated within the reaction vessel via a centrifugation pump.

D. A system for biomethanation in which a microbial population produces methane using carbon dioxide and hydrogen as substrates, wherein the system comprises a reaction vessel, said reaction vessel comprising at least one inlet for enabling carbon dioxide and hydrogen to enter the reaction vessel, and further comprising a liquid medium within said reaction vessel, wherein said liquid medium is circulated continuously within the reaction vessel via means of a pump, and wherein said pump sucks in said gases entering the reaction vessel as said gases enters said reaction vessel, or shortly thereafter, so that said gases mix with said liquid medium and form microbubbles. In some embodiments said gases comprise a gaseous composition comprising carbon dioxide and any of carbon monoxide, hydrogen, nitrogen, and one or more hydrocarbons, along with any trace components contained therein. In some embodiments said pump is a centrifugation pump.

E. A system for biomethanation in which a microbial population produces methane using carbon dioxide and hydrogen as substrates, wherein the system comprises a reaction vessel comprising a liquid medium, wherein the production of methane by said microbial population comprises the production of water as a by-product, and wherein said system comprises means for removing excess water without removing nutrients and microbes from said liquid medium. In some embodiments, the removal of excess water is achieved without removing nutrients and microbes from the reaction vessel. In some embodiments, the removal of excess water is via evaporation. In some embodiments the removal of excess water is via osmosis. In some embodiments, said means for removing excess water comprises a fan or suction or blowing device for withdrawing gas from the headspace of said reaction vessel, passing said gas through said a condensing or desiccating unit, and returning said gas to the headspace in said reaction vessel. In some embodiments said means for removing excess water comprises a container comprising a solution with salt concentration of greater osmotic potential than that of said liquid medium, said container being attached to said reaction vessel by a port comprising an osmosis membrane with a pore size of less than 5 angstroms, wherein the salt concentration is adjusted to control the degree to which water moves from said reaction vessel into said container. In some embodiments, said means for removing excess water comprises a filtration device comprising a series of filters of decreasing pore size, said filtration device being connected to a port on said reaction vessel, wherein said system comprises a pump capable of driving the liquid through said filtration device towards a tank; in some embodiments, said filters comprise one or more of a particle filter, a micro-filter, an ultra-filter, a nano-filter and a filter permitting reverse osmosis; in some embodiments, said pump is a reversible pump.

The above embodiments are to be understood as illustrative examples of the invention. Further embodiments of the invention are envisaged. It is to be understood that any feature described in relation to any one embodiment may be used alone, or in combination with other features described, and may also be used in combination with one or more features of any other of the embodiments, or any combination of any other of the embodiments. Furthermore, equivalents and modifications not described above may also be employed without departing from the scope of the invention, which is defined in the accompanying claims.

What is claimed is:

1. A method of converting hydrogen and at least one of carbon dioxide and carbon monoxide to methane, comprising:

degrading microbial cells and converting hydrogen and at least one of carbon dioxide and carbon monoxide to methane within a reaction vessel; said reaction vessel comprising at least one inlet to pass in to the reaction vessel, hydrogen, and at least one of carbon monoxide and carbon dioxide;

providing a microbial population in a liquid medium in said reaction vessel; said microbial population comprising:

one or more species of hydrogenotrophic methanogens;
one or more species of hydrolytic microbes;
one or more species of acidogenic microbes,
one or more species of acetogenic microbes; and
one or more species of acetoclastic microbes; and
said liquid medium comprising:
a group of nutrients consisting of:
- aluminium, wherein the aluminium is present in an amount of at least 0.01 mg/l;
- boron, wherein the boron is present in an amount of at least 0.01 mg/l;
- calcium, wherein the calcium is present in an amount of at least 2.0 mg/l;
- cobalt, wherein the cobalt is present in a range of between 0.05 mg/l and 1 mg/l;
- copper, wherein the copper is present in a range of between 0.01 mg/l and 4 mg/l;
- iron, wherein the iron is present in an amount of at least 0.5 mg/l;
- potassium, wherein the potassium is present in an amount of at least 50 mg/l;
- magnesium, wherein the magnesium is present in an amount of at least 20 mg/l;
- manganese, wherein the manganese is present in a range of 0.05 mg/l and 6 mg/l;
- molybdenum, wherein the molybdenum is present in a range of 0.05 mg/l and 1.5 mg/l;
- nickel, wherein the nickel is present in a range of 0.05 mg/l and 6 mg/l;
- phosphorus, wherein the phosphorus is present in an amount of at least 25 mg/l;
- sulphur, wherein the sulphur is present in an amount of at least 25 mg/l;
- selenium, wherein the selenium is present in a range of 0.05 mg/l and 1.5 mg/l;
- sodium, wherein the sodium is present in an amount of at least 40 mg/l;
- tungsten, wherein the tungsten is present in a range of 0.05 mg/l and 1.5 mg/l;
- vanadium, wherein the vanadium is present in a range of 0.03 mg/l and 1.5 mg/l and
- zinc, wherein the zinc is present in a range of 0.03 mg/l and 9 mg/l; and degrading dead microbial cells and releasing nutrients from the dead microbial cells to said medium, thereby maintaining a total amount of nutrients in said medium within said range relative to the amount of water and total solids within said medium, without the addition of one or more nutrients to said medium, for a period of at least 7 days;
and feeding said medium only with one or more of: hydrogen, and one or more of carbon monoxide and carbon dioxide.

2. The method of claim 1, the at least one inlet enabling carbon dioxide; hydrogen; and a gaseous composition comprising carbon monoxide, carbon dioxide, hydrogen, nitrogen, or a combination thereof; and one or more hydrocarbons, to pass into the reaction vessel.

3. The method of claim 2, further comprising:
measuring the levels of at least one of methane, carbon dioxide, and hydrogen in said gaseous composition; and
adjusting the flow of at least one of the gaseous composition, carbon dioxide, and hydrogen into the reaction vessel to maintain at least one desired parameter within the reaction vessel.

4. The method of claim 3, wherein the gaseous composition is carbon dioxide, and wherein adjusting the flow of said carbon dioxide into the reaction vessel maintains at least one desired parameter within the reaction vessel.

5. The method of claim 4, wherein the at least one desired parameter is a pH of the liquid medium within said reaction vessel.

6. The method of claim 1, wherein said period is at least 14 days.

7. The method of claim 1, wherein said period is at least 28 days.

8. The method of claim 1, wherein the period is at least 48 days.

9. The method of claim 1, wherein the period is at least 96 days.

10. The method of claim 1, wherein said period is the length of time in which a reactor into which said medium is placed is operational.

11. The method of claim 2, further comprising:
monitoring said reaction vessel; and
removing excess water when the amount of liquid in said reaction vessel reaches or exceeds a predetermined level.

\* \* \* \* \*